(12) United States Patent
Shahar et al.

(10) Patent No.: US 9,261,611 B2
(45) Date of Patent: Feb. 16, 2016

(54) SYSTEMS AND METHODS FOR SCANNING WITH RADIATION DETECTORS

(71) Applicant: General Electric Company, Schenectady, NY (US)

(72) Inventors: Arie Shahar, Moshav Magshimim (IL); Eliezer Traub, Ramat-Gan (IL)

(73) Assignee: General Electric Company, Schenectady, NY (US)

( * ) Notice: Subject to any disclaimer, the term of this patent is extended or adjusted under 35 U.S.C. 154(b) by 341 days.

(21) Appl. No.: 13/624,660

(22) Filed: Sep. 21, 2012

(65) Prior Publication Data
US 2014/0084171 A1    Mar. 27, 2014

(51) Int. Cl.
*G01T 1/29* (2006.01)
*G01T 1/164* (2006.01)
*A61B 6/00* (2006.01)
*A61B 6/03* (2006.01)

(52) U.S. Cl.
CPC ............. *G01T 1/2985* (2013.01); *A61B 6/4291* (2013.01); *G01T 1/1648* (2013.01); *A61B 6/032* (2013.01); *A61B 6/037* (2013.01); *A61B 6/5205* (2013.01); *A61B 6/542* (2013.01)

(58) Field of Classification Search
CPC ................ G01T 1/20; G01T 1/00; G01T 1/17
USPC ........... 250/363.05, 394, 395, 363.1, 370.09, 250/370.13, 370.1, 370.08; 378/901, 4
See application file for complete search history.

(56) References Cited

U.S. PATENT DOCUMENTS

| | | | | |
|---|---|---|---|---|
| 3,585,387 | A * | 6/1971 | Bramlet | 250/363.01 |
| 3,869,615 | A * | 3/1975 | Hoover et al. | 378/146 |
| 3,946,984 | A * | 3/1976 | Sutter | 251/129.03 |
| 4,259,578 | A * | 3/1981 | Thompson | 250/363.03 |
| 4,259,587 | A * | 3/1981 | Takahashi et al. | 250/486.1 |
| 4,755,680 | A * | 7/1988 | Logan | 250/363.01 |
| 4,849,638 | A * | 7/1989 | Hawman | 250/363.02 |
| 4,905,268 | A | 2/1990 | Mattson et al. | |
| 5,591,976 | A * | 1/1997 | Berthold et al. | 250/363.1 |
| 5,740,222 | A * | 4/1998 | Fujita et al. | 378/4 |
| 6,054,712 | A | 4/2000 | Komardin et al. | |
| 6,353,227 | B1 * | 3/2002 | Boxen | 250/363.1 |
| 6,525,320 | B1 * | 2/2003 | Juni | 250/363.04 |
| 6,649,914 | B1 * | 11/2003 | Moorman et al. | 250/363.06 |
| 7,310,407 | B2 * | 12/2007 | Juni | 378/63 |
| 7,439,514 | B1 | 10/2008 | Uribe et al. | |
| 7,663,111 | B2 | 2/2010 | Shahar et al. | |

(Continued)

*Primary Examiner* — David Porta
*Assistant Examiner* — Blake Riddick
(74) *Attorney, Agent, or Firm* — Dean D. Small; The Small Patent Law Group, LLC.

(57) ABSTRACT

Systems and methods for scanning with radiation detectors are provided. One system includes at least one radiation scanning camera-head, an array of at least one pixelated radiation detector having an imaging surface including a two dimensional array of pixels, and a scanning unit positioned between the radiation detector and the object. The scanning unit includes first and second radiation blocking plates having first and second two-dimensional arrays of openings, respectively, wherein the array of pixels and the first and second arrays of openings have a same pitch. Additionally, for each of a plurality of scan positions of the scanning unit, the first and second moveable plates and the imaging surface are positioned differently with respect to each other to produce different inclination angles in response to each scan position.

29 Claims, 20 Drawing Sheets

(56) References Cited

U.S. PATENT DOCUMENTS

| | | |
|---|---|---|
| 8,199,884 B2 | 6/2012 | Junjie et al. |
| 8,213,568 B2 | 7/2012 | Heuscher et al. |
| 2001/0005409 A1* | 6/2001 | Gohno et al. ............. 378/19 |
| 2002/0075990 A1* | 6/2002 | Lanza et al. ............... 378/2 |
| 2004/0264626 A1* | 12/2004 | Besson ....................... 378/4 |
| 2007/0188765 A1* | 8/2007 | Zhao et al. ............... 356/479 |
| 2008/0073599 A1 | 3/2008 | Vija |
| 2008/0237476 A1* | 10/2008 | Uribe et al. ............. 250/363.04 |
| 2008/0237482 A1* | 10/2008 | Shahar et al. ............. 250/394 |
| 2009/0190714 A1* | 7/2009 | Partain ....................... 378/19 |
| 2010/0005409 A1* | 1/2010 | Ratzlaff et al. ............. 715/765 |
| 2010/0329419 A1* | 12/2010 | Blevis ......................... 378/37 |
| 2011/0096970 A1* | 4/2011 | Vija ........................... 382/131 |
| 2012/0069954 A1 | 3/2012 | Iso et al. |
| 2012/0219107 A1 | 8/2012 | Kurochi et al. |

\* cited by examiner

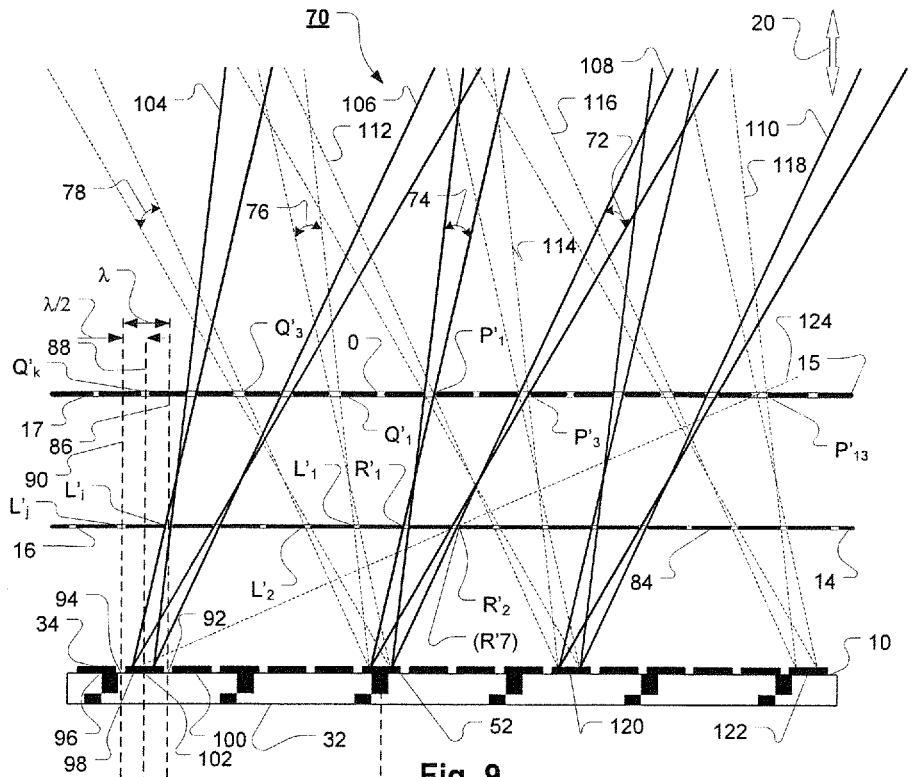
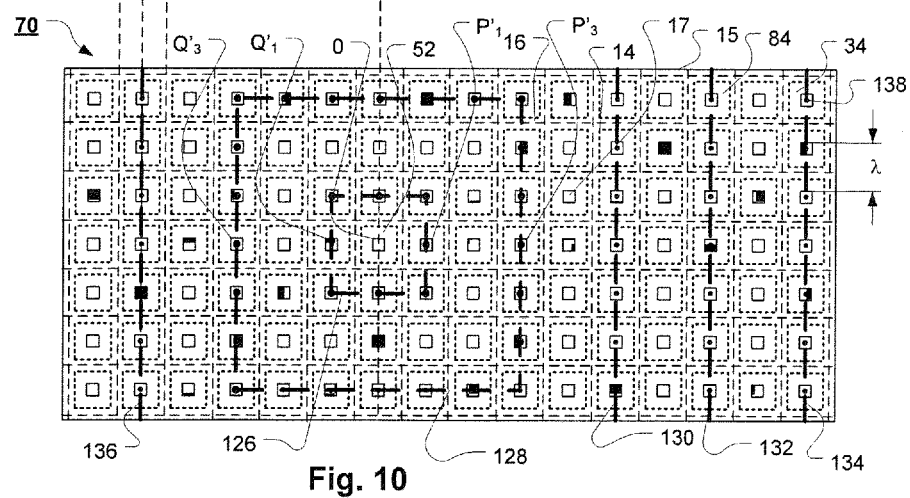

SYSTEMS AND METHODS FOR SCANNING WITH RADIATION DETECTORS

BACKGROUND OF THE INVENTION

The subject matter disclosed herein relates generally to systems and methods for the detection of ionizing radiation, such as gamma-ray and X-ray radiation, and more specifically to scanning systems and methods of radiation detection for medical diagnosis including Single Photon Counting Tomography (SPECT).

Different scanning methods are known for use in detecting ionizing radiations, such as systems that use variable collimators. For example, some known methods of three dimensional (3D) image reconstruction use multiple image-acquisitions with different collimations of the imaging-collimator, such as by changing the collimation of the imaging-collimator. These systems use forward looking variable collimators constructed from multiple collimation elements where each collimation element may be varied and may produce multiple corresponding viewing-angles with a primary axis that is normal to imaging planes produced by detectors. These imaging planes are behind the collimators and arranged to receive the radiation emitted from an imaged object via the collimators. The structures of the collimators and collimation elements are designed to reduce or avoid any crosstalk of radiation between the collimation elements, for example, to prevent or reduce the likelihood of gamma rays passing through the gap of one septum into another collimator aperture.

Additionally, the different viewing angles produced by the variable collimation elements are included in each other in a way that each viewing angle contains all the viewing angles that are smaller than this viewing angle. As a result, acquisition of multiple images using variable collimators using conventional systems creates a significant redundancy of information in which the same information appearing in one image appears in another images as well. In some of the images, the repeated information is the major information and only a small fraction in these images is new information that does not appear in other images.

In order to increase the sensitivity of the imaging system, each of the multiple images acquired in different collimation of the imaging-collimator includes the imaged region. This imaged region is on and in the imaged object and is significantly larger than the size of the desired spatial resolution. The reconstruction of the image within the desired spatial resolution is produced by various image-reconstruction methods which include intensive mathematical calculations based on multiple equations derived from the multiple images. For example, in some systems, the number of images acquired for reconstructing a SPECT image times the number of pixels in each image is equal to the number of virtual voxels into which the imaged object is to be divided. Accordingly, the large size of the imaged region, on the imaged object, in each acquired image and the large number of acquired images that is needed for the 3D image reconstruction does not allow for selecting only images acquired with no information redundancy.

Moreover, the redundancy of the acquired information increases the statistical error in the equations that contain the repeated information without adding new information useful for the image reconstruction. Also, the equations in which the repeated information is significant are dependent equations and do not contribute insignificant information for the image reconstruction. The redundant or repeated information in general and especially the redundant or repeated information in the dependent equations, contribute mainly statistical errors without any substantial new information. These statistical errors are enhanced by the intensive mathematical calculations involved in the image-reconstruction methods.

Thus, the reconstruction of images using some known systems and methods includes repetitive information that enhances the statistical errors when using the algorithm for image reconstruction. Thus, reconstructed images may suffer from poor quality and may also include reconstruction artifacts.

BRIEF DESCRIPTION OF THE INVENTION

In accordance with one embodiment, a system for scanning and collecting ionizing radiation emitted from an object is provided. The system includes at least one radiation scanning camera-head, an array of at least one pixelated radiation detector having an imaging surface including a two dimensional array of pixels, and a scanning unit positioned between the radiation detector and the object. The scanning unit includes first and second radiation blocking plates having first and second two-dimensional arrays of openings, respectively, wherein the array of pixels and the first and second arrays of openings have a same pitch. Additionally, projections of the openings of the first array onto the imaging surface of the pixelated radiation detector are aligned with border lines between adjacent pixels and projections of the openings of the second array onto the imaging surface of the pixelated radiation detector are aligned with centers of the pixels to produce radiation paths from the object to the pixelated radiation detector via the first and second arrays of openings. Also, the radiation paths are oriented along lines forming inclination angles with lines oriented normal to the imaging surface and the first and second plates are movable along a direction normal to the imaging plane to perform a linear scan of the scan unit. Further, for each of a plurality of scan positions of the scanning unit, the first and second moveable plates and the imaging surface are positioned differently with respect to each other to produce different inclination angles in response to each scan position.

In accordance with another embodiment, a method for scanning and collecting ionizing radiation emitted from an object is provided. The method includes configuring and controlling a scanning unit as described above.

BRIEF DESCRIPTION OF THE DRAWINGS

FIGS. 8 and 9 are schematic illustrations of the side-views of multiple non-forward scanning angles produced by scanning units in accordance with various embodiments illustrating the corresponding collimations and directions of the scanning angles.

FIGS. 10-13 are schematic top-views illustrations of the radiation-blocking scanning-plates of the scanning units shown in FIGS. 3 and 4, including their openings.

DETAILED DESCRIPTION OF THE INVENTION

Figure 1:
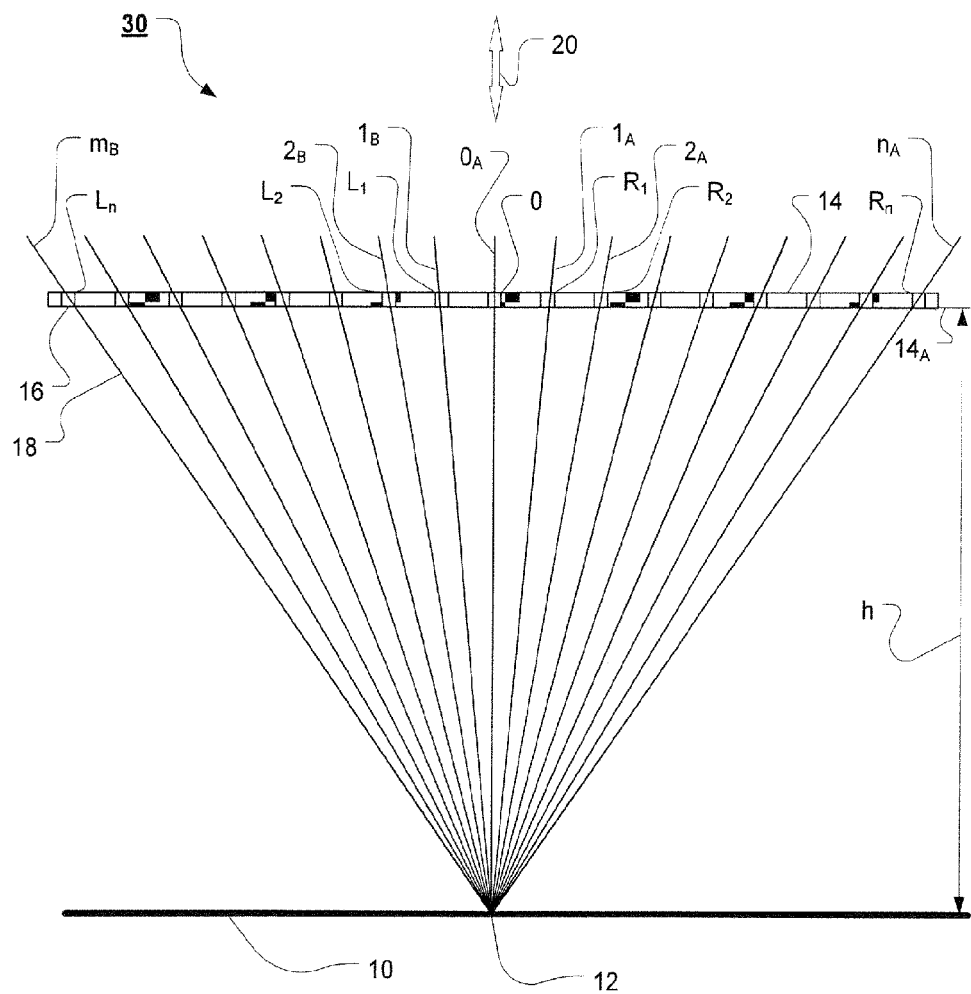
FIGS. 1-5 are schematic side-view diagrams illustrating a radiation scan unit including one movable radiation blocking plate having an array of openings shown in various scan positions in accordance with various embodiments.

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

Various embodiments provide systems and methods for non-forward wide-angle and high-sensitivity two-dimensional (2D) scanning for radiation detectors, such as Single Photon Emission Computed Tomography (SPECT) detectors. However, the various embodiments may be implemented in different types of detectors, such as radiation detectors for detecting ionizing radiation (e.g., gamma-ray or X-ray radiation).

At least one technical effect of various embodiments is acquiring images with high sensitivity and/or allowing high quality image-reconstruction of an imaged object. At least one other technical effect of various embodiments is providing a scan system having imaging-collimator including variable collimation elements.

Some embodiments provide a scan system including a pixelated detector array in which the number of collimation elements in the radiation scanning-unit is the same or similar to the number of pixels in the pixelated detector array. The radiation scanning unit may have collimation elements that include pinholes. Additionally, in some embodiments, the scan system is configured to acquire multiple images of the imaged object that are substantially different from each other to allow, for example, for high quality image-reconstruction of the imaged object. In various embodiments, a radiation scanning unit may be provided having imaging-elements including variable collimation elements wherein for each scan setting of the scanning unit, there is a corresponding image of the imaged object acquired by the pixelated detector via the imaging scanning-unit and wherein this image is substantially different for different scan settings. The scan unit in some embodiments is capable of two-dimensional (2D) scanning.

In other embodiments, an angular scanning system may be provided having imaging-elements including radiation directional-scanning elements wherein for each collimation and directional setting of the angular scanning system, there is a corresponding two-dimensional angular scanning to produce a corresponding image that is substantially different for different scanning angles. In still other embodiments, a scan system may be provided having an imaging-unit including variable collimation and directional elements wherein for each collimation and directional setting of the collimation and directional elements, there is a corresponding two-dimensional scanning angle for producing a corresponding image that is substantially different for different scanning angles even when the scanning angles are relatively large.

More particularly, FIGS. 1-5 schematically illustrate a side view of a scanning unit 30 that may form part of one or more scanning systems (as described in more detail herein) using variable collimation of an array of pinholes formed in a movable plate that is capable of changing a position thereof relative to an imaging plane of an array of radiation detectors. It should be appreciated that when reference is made herein to variable collimation, this refers to both a variable solid viewing angle and a variable direction of the viewing angle.

FIG. 1 schematically illustrates that scanning unit 30 including an imaging plane 10 formed by radiation detectors (not shown) designed to detect ionizing radiation such as gamma ray and/or X-ray photons. The imaging plane 10 may represent the imaging plane of a camera head or camera heads designed to produce medical diagnosis in the field of medical imaging including SPECT applications. The detectors may be produced from semiconductor material, such as Cadmium Zinc Telluride (CdZnTe or CZT) and may be in the form of pixelated detector array in various embodiments.

A point 12 on the imaging plane 10 schematically represents any viewing point looking toward an imaged object (not shown) via an array 16 of pinholes in a plate 14. The plate 14 in various embodiments is made of a material and has a thickness that blocks the ionizing radiation arriving from the direction of the imaged object. For example, the plate 14 may be formed form a high absorption material such as Lead (Pb) or Tungsten (W). The position of the plate 14 is indicated by position $14_A$. The scanning solid viewing-angles (see FIGS. 6-9) through which the point 12 on the imaging plane 10 looks at the imaged or scanned object via the pinholes 16 are indicated by the primary axes 18.

The pinholes 16 are indicated by 0 for the central pinhole directly above the point 12 and all the pinholes located to the right and to the left of pinhole 0 are marked by the letters R (that stand for Right) and L (that stand for Left), respectively, with the additional counting index that represents the position of the pinholes relative to the central pinhole 0. For example, the first, second and $n^{th}$ pinholes to the right of pinhole 0 are marked $R_1$, $R_2$ and $R_n$, respectively. Similarly, the first, second and $m^{th}$ pinholes to the left of pinhole 0 are marked $L_1$, $L_2$ and $L_m$, respectively.

The primary axes 18 are indicated by $0_A$ for the central primary axis passing through pinhole 0. All other primary axes 18 located to the right and to the left of the primary axis $0_A$ are marked by a counting index that represents the position of primary axes 18 relative to central primary axis $0_A$. In addition to the counting index of the primary axes 18, the additional index letter A or B indicates that the primary axes 18 are to the right or left to axis $0_A$, respectively. For example, the first, second and $n^{th}$ primary axes 18 to the right of primary axis $0_A$, which pass through pinholes $R_1$, $R_2$ and $R_n$, are marked $1_A$, $2_A$ and $n_A$, respectively. Similarly, the first, second and $m^{th}$ primary axes 18 to the left of pinhole $0_A$, which pass through pinholes $L_1$, $L_2$ and $L_m$, are marked $1_B$, $2_B$ and $m_B$, respectively.

The pinhole plate 14 is movable along arrows 20, by a moving mechanism or means (not shown), for changing the distance h between the imaging plane 10 and the plate 14 located at position $14_A$. In one embodiment, an angular scan of variable scanning angles having the primary axes 18 is achieved by a linear scan of the plate 14 changing the distance h between the pinholes 14 and the imaging plane 10.

It should be noted that the same referral numerals are used to indicate similar parts and features in the different Figures.

Figure 2:
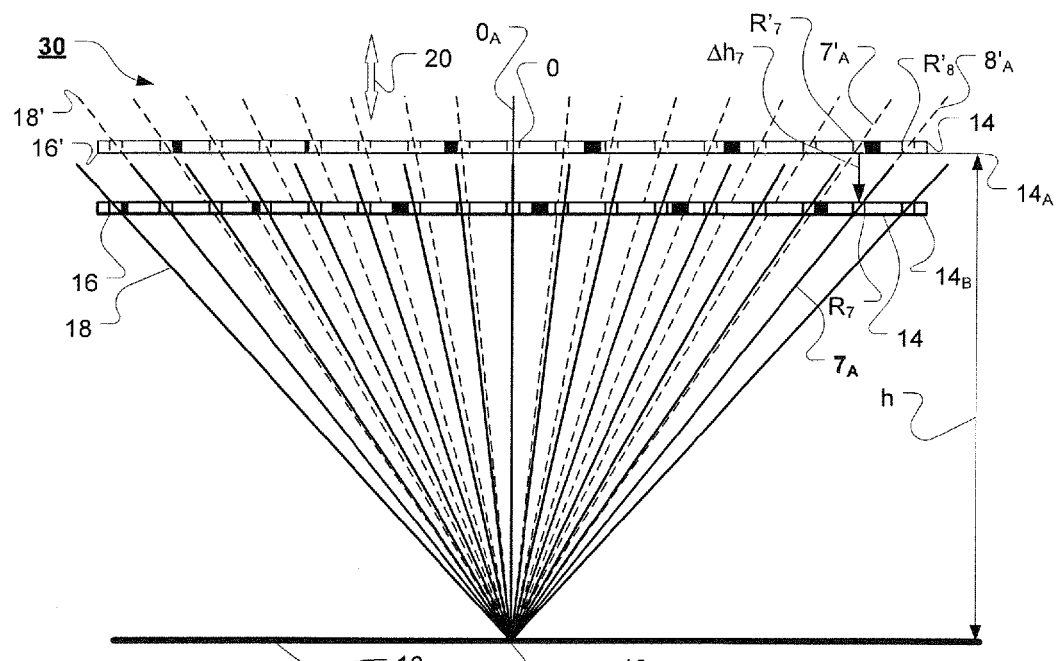

FIG. 2 schematically illustrates a side view of the scanning unit 30 where the plate 14 (also referred to as the pinhole-plate) is shown in two positions indicated as positions $14_A$ and $14_B$. In the first position $14_A$ of the pinhole-plate 14 (illustrated by broken lines), the primary axes 18', shown by broken lines, pass from the point 12 on the imaging plane 10 toward an imaged object (not shown) via the 16' of the plate 14. In the second position $14_B$ of the pinhole-plate 14 (illustrated by solid lines) the primary axes 18, shown by solid lines, pass from the point 12 on the imaging plane 10 toward an imaged object (not shown) via the pinholes 16 of the plate 14.

It can be seen that while the pinhole-plate 14 moves, along arrows 20 and normal to imaging plane 10, from a first position at $14_A$ to a second position at $14_B$, the primary axes 18' of the viewing solid angles at the position $14_A$ produce an angular scan by moving to appear as the primary axes 18 in another rotational angle corresponding to the second scan position $14_B$ of the pinhole-plate 14. The primary axis $0_A$ does not change orientation, but all other primary axes 18' increase a corresponding inclination angles relative to the primary axis $0_A$, which is oriented normal to the imaging plane 10, to perform the angular scan, while the pinhole-plate 14 moves from the first scanning position $14_A$ to the second scanning position $14_B$.

For example, the primary axis $7'_A$ passing through the $R'_7$ when the pinhole-plate 14 is in the first position $14_A$, produces an angular scan to appear as the primary axis $7_A$ passing through the pinhole $R_7$, while the pinhole-plate 14 moves to the second position $14_B$. At the first scan position of the plate $14_A$, the pinhole-plate 14 is located at a distance h from the imaging plane 10. After pinhole-plate 14 moved a distance of $\Delta h_7$ toward imaging plane 10 and along arrows 20, pinhole $R'_7$ in position $14_A$ moves to appear as pinhole $R_7$ in position $14_B$ through which primary axis $7_A$ passes through.

It can be seen that primary axis $7_A$ passing via pinhole $R_7$ in position $14_B$ is on the same line of primary axis $8'_A$ passing via pinhole $R'_8$ in position $14_A$. Accordingly, if the pinhole-plate 14 moves further along the arrows 20 at a distance larger than $\Delta h_7$, the primary axis $7_A$ performs an angular scan along the same range already scanned by the axis $8'_A$ when the pinhole-plate 14 already moved in the range of $\Delta h_7$ when changing position from position $14_A$ to position $14_B$.

Thus, for each pinhole in the pinhole-plate 14 there is a specific scan range that beyond this range, the angular scan range may repeat the scan range already scanned previously by other pinholes located next to this pinhole (having higher counting index or located farer from pinhole 0). In the example illustrated by FIG. 2, the scan range $\Delta h_7$ of the pinhole $R'_7$ (located in the pinhole-plate 14 when located at the position $14_A$) is in the ranges that beyond this scan range, the pinhole $R_7$ (located in the pinhole-plate 14 when at position $14_B$) starts to repeat the scan range of pinhole $R'_8$. Repeating the scan range produces information redundancy in the image acquisition and this information redundancy does not contribute to the image reconstruction, but enhances the statistical noise in the image and may contribute to errors that may produce low quality and artifacts in the reconstructed image.

As discussed above, FIG. 2 schematically illustrates the maximum scan range $\Delta h_7$ of the pinhole $R'_7$ along the arrows 20, which still ensures that there is no information redundancy in the scan between the pinhole $R'_7$ and the other pinholes 16'. Similar to FIG. 2, FIG. 3 shows the maximum scan range $\Delta h_1$ of the pinhole $R'_1$ along the arrows 20, which still ensures that there is no information redundancy (repetitive information) in the scan between pinhole the $R'_1$ and the other pinholes 16'.

Figure 3:
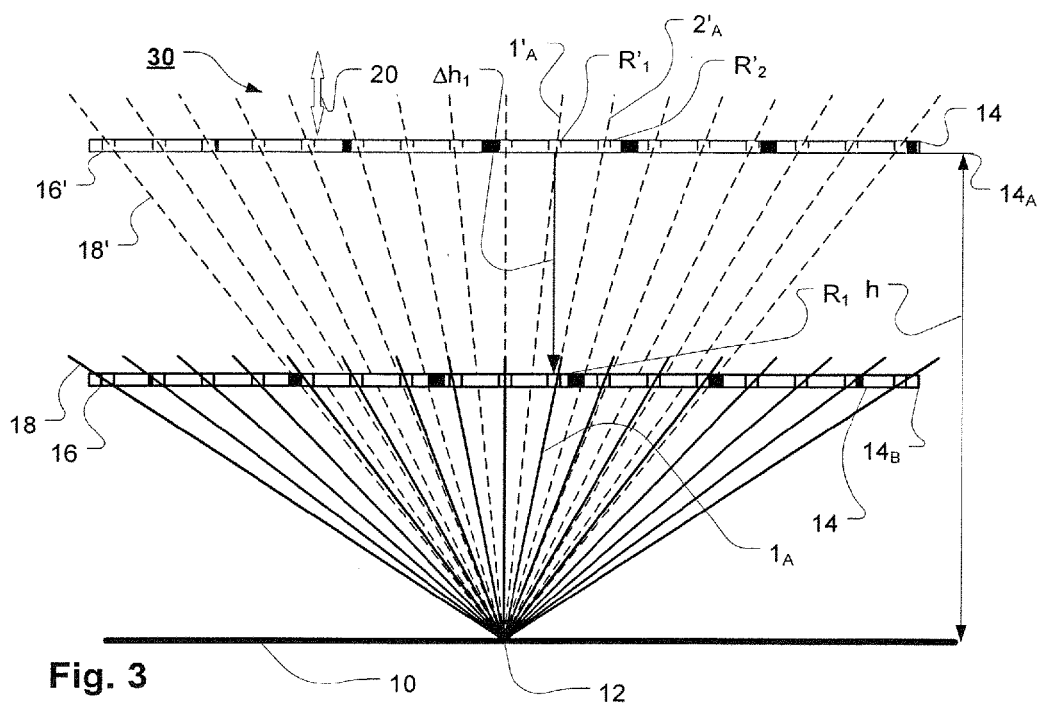

From FIG. 3, which is a schematic illustration of the side view of the scanning system 30, it can be seen that while the pinhole-plate 14, moves along the arrows 20, from the first position at $14_A$ to the second position at $14_B$, the primary axes 18' of the viewing solid angles at position $14_A$ produce an angular scan by moving to appear as the primary axes 18 when the pinhole-plate 14 reaches the second scan position $14_B$. The primary axis $0_A$ does not change orientation, but all the other primary axes 18' increase a corresponding inclination angle relative to the primary axis $0_A$ to perform the angular scan while the pinhole-plate 14 moves from the first scanning position $14_A$ to the second scanning position $14_B$. For example, the primary axis $1'_A$ passing through the $R'_1$ when the pinhole-plate 14 is in the first scan position $14_A$, produces an angular scan to appear as the axis $1_A$ passing through the pinhole $R_1$ while the pinhole-plate 14 moves to the second scan position $14_B$.

At the first position $14_A$, the pinhole-plate 14 is located at a distance h from imaging plane 10. After the pinhole-plate 14 is moved a distance of $\Delta h_1$ toward the imaging plane 10 along the arrows 20 and normal to the imaging plane 10, the pinhole $R'_1$ in the position $14_A$ moves to appear as the pinhole $R_1$ in the position $14_B$ through which the primary axis $1_A$ passes.

It can be seen that the primary axis $1_A$ passing via the pinhole $R_1$ in the position $14_B$ is on the same line of the primary axis $2'_A$ passing via the pinhole $R'_2$ in the position $14_A$. Accordingly, if the pinhole-plate 14 moves further along the arrows 20 at a distance larger than $\Delta h_1$, the primary axis $1_A$ performs a repetitive angular scan along the same range already scanned by the primary axis $2'_A$ when the pinhole-plate 14 already moved in the range of $\Delta h_1$ when changing position from the position $14_A$ to the position $14_B$. Accordingly, in general, for any pinhole $R'_j$, when j is an integer index, the scan range $\Delta h_j$ is actually the non-repetitive scan range of the pinhole $R'_j$ indicating the maximum scan range of the plate 14 along the arrows 20 in which the angular scan via the pinhole $R'_j$ still is not performed by the other pinholes 16' having a counting index higher than j.

Figure 4:
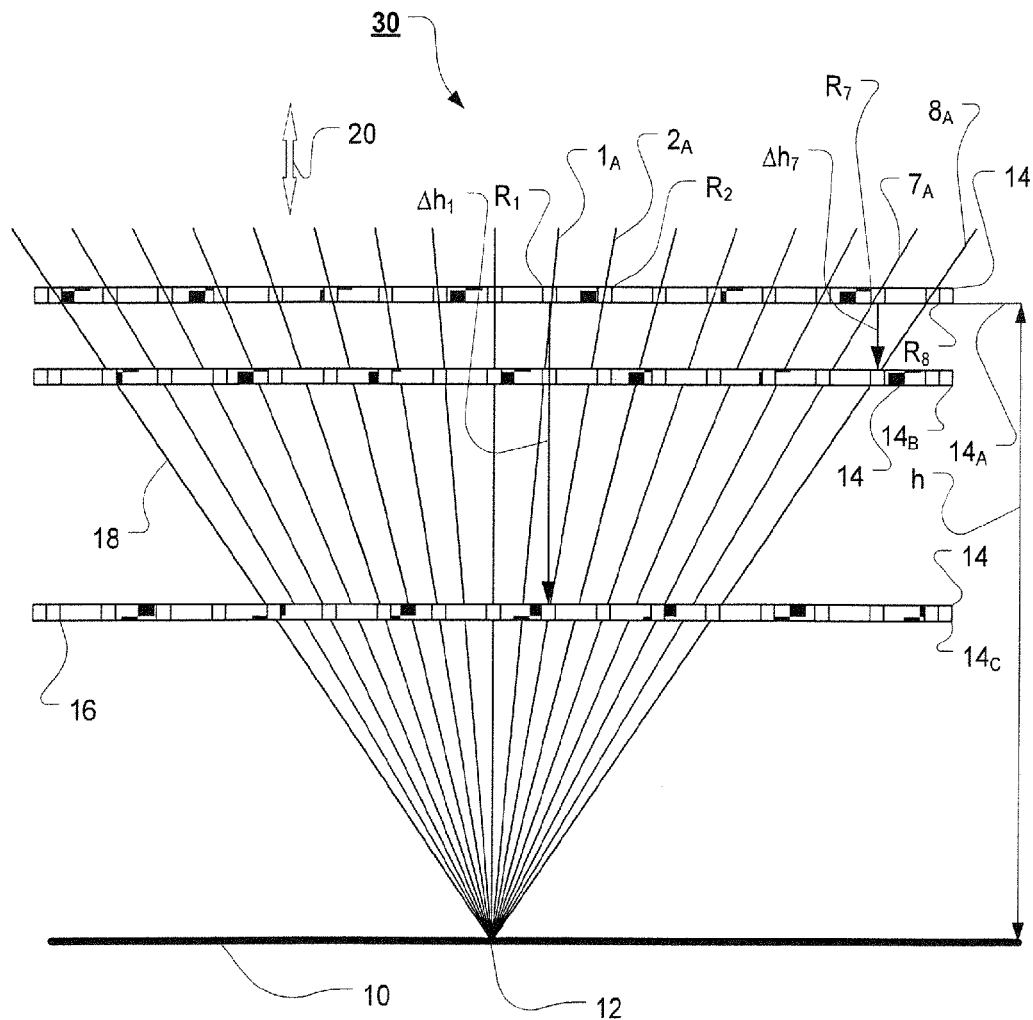

FIG. 4 combines FIGS. 2 and 3 into one drawing for schematic demonstration of the proportion between scanning distances $\Delta h_1$ and $\Delta h_7$. The first and second positions $14_A$ and $14_B$ of the pinhole-plate 14, respectively, are the same for FIGS. 2 and 3. The first and second positions $14_A$ and $14_B$ of the pinhole-plate 14, respectively, in FIG. 3 appear as the first and second positions $14_A$ and $14_C$ of the pinhole-plate 14, respectively, in FIG. 4.

It can be seen that the non-repetitive scan range $\Delta h_1$ is significantly larger than the non-repetitive scan range $\Delta h_7$. Thus, the scan range still ensures that there is no repetition of the scan range between a certain pinhole and other pinholes 16' that increases with the reduction of the distance of this specific pinhole from the central pinhole 0 (proportional to the value of the counting index of pinholes 16'). Accordingly, during the scanning of the plate 14 along the non-repetitive scan range $\Delta h_1$, the pinhole $R'_7$ or other the pinholes 16' having counting index j>1 corresponding to the non-repetitive scan range $\Delta h_j$ may produce several repetitive scans. This situation is expressed in general for any indices j and k of the pinholes 16', by the mathematical relations:

$$\Delta h_j > \Delta h_k \quad \text{Eq (1)}$$

when j<k

Figure 5:
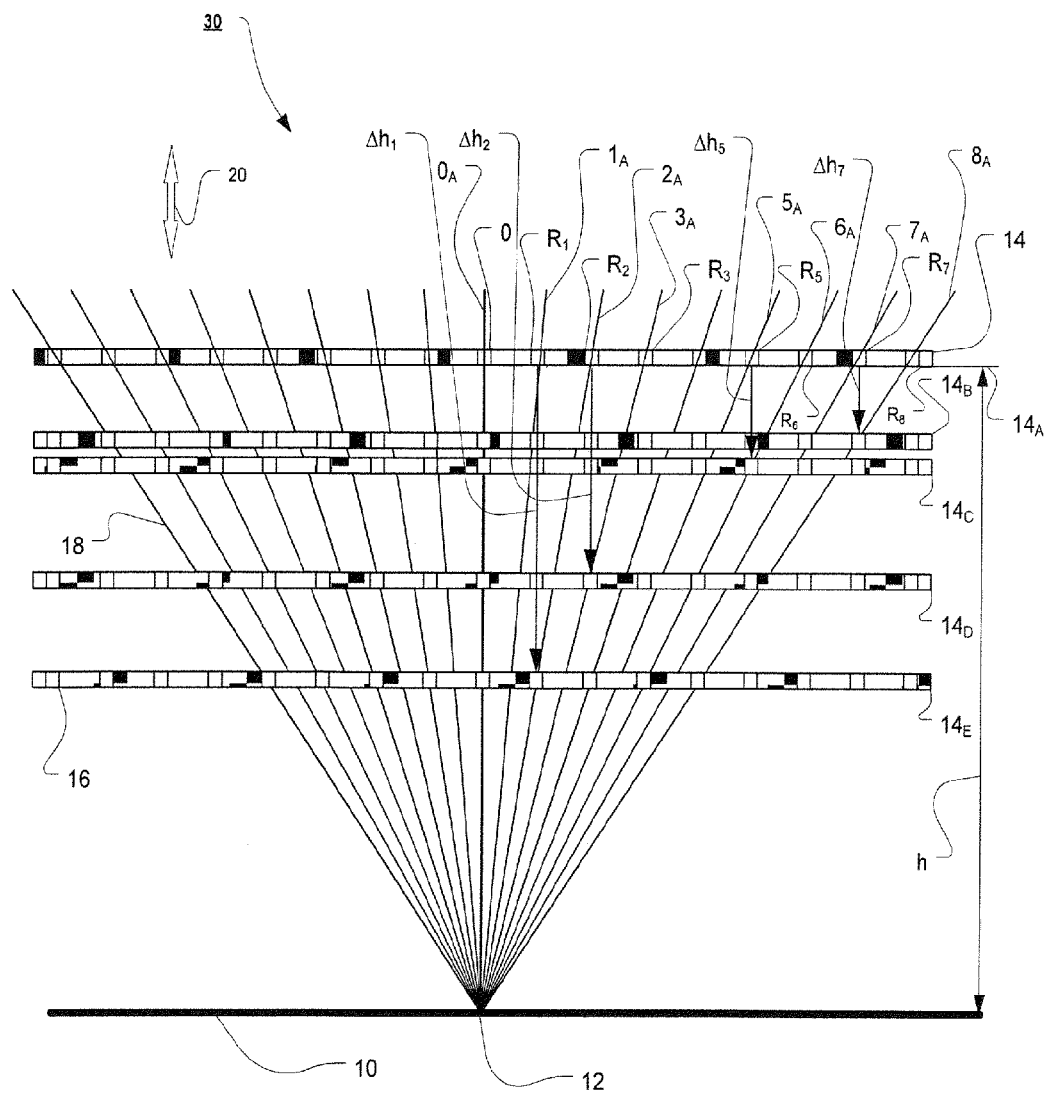

FIG. 5 is a schematic illustration of the scanning unit 30 showing the pinhole-plate 14 in several scanning positions $14_A, 14_B, 14_C, 14_D$ and $14_E$ along the arrows 20. The operation principle of the scan of the unit 30 is symmetric around the central pinhole 0 in the illustrated embodiment. Thus, without any limitation, the description for FIG. 5 includes explanations about the portion of the scan unit 30 that is located right of the central pinhole 0, which deals specifically with the pinholes 16, such as those marked as $R_1, R_2, R_3, R_5, R_6, R_7$ and $R_8$. The respective primary axes $1_A, 2_A, 3_A, 5_A, 6_A, 7_A$ and $8_A$ of the viewing solid scanning angles (not shown) correspond to the pinholes 16 located to the left of pinhole 0 as well. It should be noted that for each point, such as the point 12 located on the imaging plane 10, the corresponding pinhole located above such a point can be marked as pinhole 0 in the coordinate system of such point.

FIG. 5 shows a graphical way to derive the non-repetitive scan displacement $\Delta h_j$ of the pinhole $R_j$ that is alternative to the graphical derivation shown in FIGS. 2-4. According to FIG. 5, the primary axes 18 passing through the pinholes 16 when the plate 14 is in the position $14_A$, are maintained fixed (or substantially fixed) in orientation while the plate 14 is shown in several scan positions $14_B, 14_C, 14_D$ and $14_E$. For example, the scanning displacements $\Delta h_1, \Delta h_2, \Delta h_5$ and $\Delta h_7$ are derived from the distances that the plate 14 moves from the position $14_A$, where the primary axes $1_A, 2_A, 3_A, 5_A, 6_A, 7_A$ and $8_A$ pass through the pinholes $R_1, R_2, R_3, R_5, R_6, R_7$ and $R_8$ and moving to positions $14_E, 14_D, 14_C$ and $14_B$ along the arrows 20 where the primary axis $2_A$ passes via the pinhole $R_1$, the primary axis $3_A$ passes via the pinhole $R_2$, the primary axis $6_A$ passes via the pinhole $R_5$ and the primary axis $7_A$ passes via the pinhole $R_8$, respectively.

In general, for any pinhole $R_j$ the respective non-repetitive scan range $\Delta h_j$ is equal to the distance between two scan positions of the pinhole-plate 14. The first scan position of the plate 14 is where the primary axis $j_A$ passes via the pinhole $R_j$ and the second scan position of the plate 14 is where the following primary axis $(j+1)_A$ passes via the same pinhole $R_j$.

As discussed above, it can be seen that the non-repetitive scanning displacements $\Delta h_1, \Delta h_2, \Delta h_5$ and $\Delta h_7$ corresponding to the pinholes $R_5, R_6, R_7$ and $R_8$, respectively, are longer as the distance from the central pinhole 0 is shorter, i.e. the smaller the counting index j of the pinhole the longer the non-repetitive scan range $\Delta h_j$. In addition, it can be seen that the differences between the non-repetitive scan ranges of adjacent pinholes is larger when these pinholes are closer to the central pinhole 0.

As described above, various embodiments avoid or reduce the likelihood of the redundancy of the scanned information, which does not contribute to the image reconstruction of the data acquired during the scan but enhance the statistical error. Accordingly, for a large linear scanning-range of the pinhole-plate 14 of the unit 30, in various embodiments, to produce a non-repetitive scan, the pinholes that are closer to central pinhole 0 are selected for producing the linear scan. At the same time, it is desirable to block the scanning viewing angles of the other pinholes that are further from the central pinhole 0 (having a larger counting index). As can be seen from Eq (1), while performing the angular scan of the primary axes 18 by the linear scanning (linear movement) of the plate 14, along the arrows 20 in the range of the non-repetitive scan $\Delta h_j$ of the pinhole j, the other pinholes having counting indexes k>j may produce a repetitive scan with redundancy of the scanned information since, the non-repetitive scanning range $\Delta h_j$ of the pinhole j is larger than the non-repetitive scan $\Delta h_k$ of the pinholes k.

Figure 6:
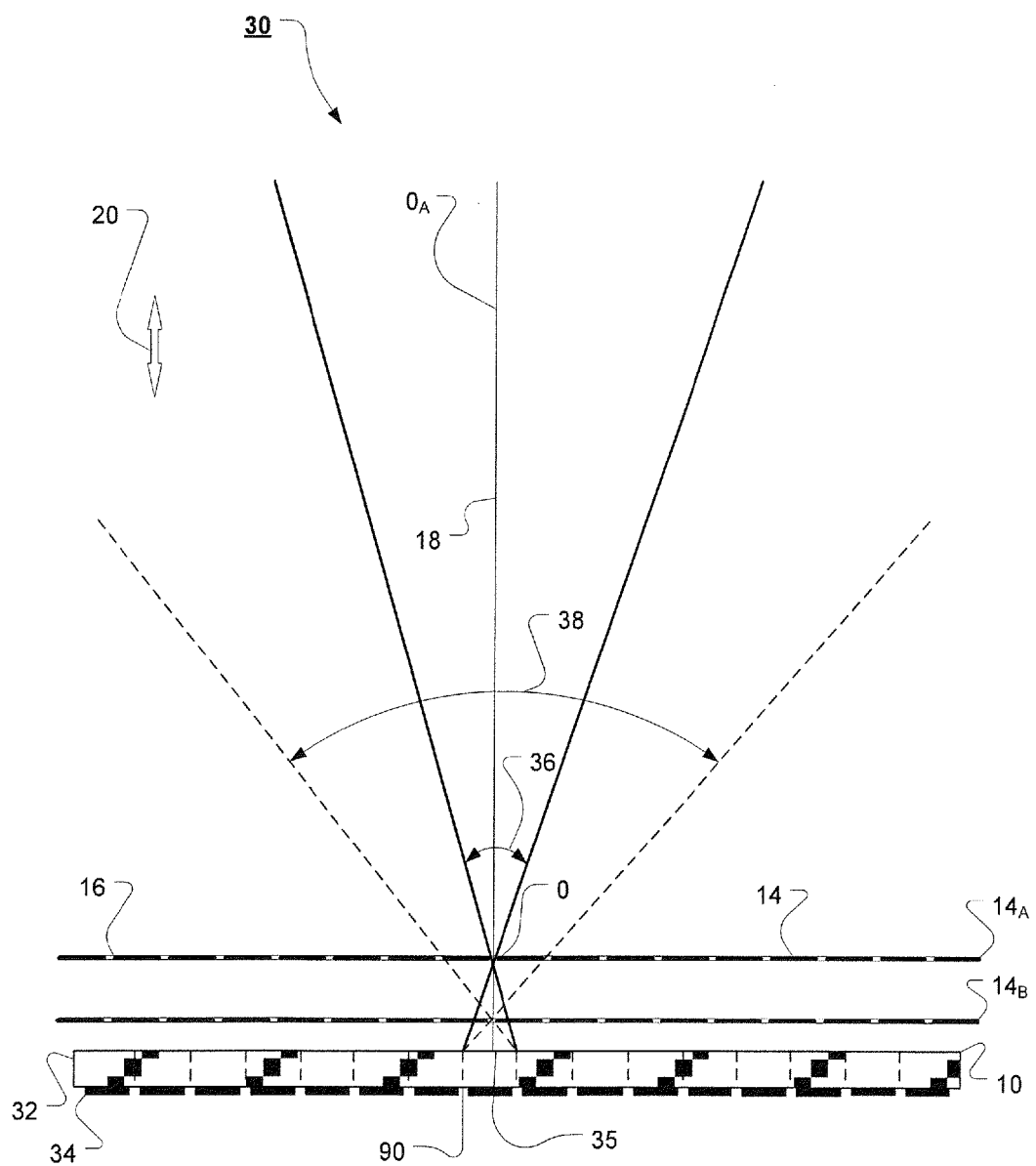
FIGS. 6 and 7 are side-views of forward and non-forward scanning angles of the scanning units of FIGS. 1-5 in two scanning positions illustrating the corresponding collimations and directions of the scanning angles, respectively.

FIG. 6 is a schematic illustration of a side view of the scanning system 30 showing scanning viewing-angles 36 and 38 produced by the pinhole-plate 14 in scanning positions $14_A$ and $14_B$, respectively. The pinhole-plate 14 is placed between the imaging plane 10 of a pixelated detector 32 having pixels 34 and the imaged object (not shown). It should be noted that, in FIG. 6 and in the other figures, reference to the pixels 34 may include the surface of the pixel on the detector plane, which may also include the whole volume of the pixel, also known as the voxel, confined between the lines 90 indicating the border lines between the pixels 34. In this case, even though the pixelated anodes of the pixels 34 may be located at the lower surface of the detector 32, these pixels still may form the imaging plane 10 on the top surface of the detector 32. The pinhole 0 is aligned to the center of the pixel 35. Additionally, the pixelated detector 32 may be produced from semiconductor materials such as CZT.

In operation, the solid scanning viewing-angle 36 of the unit 30, having the primary axis 18 marked as $0_A$, is the forward viewing scanning-angle via the pinhole 0 of the pixel 35 when the scanning pinhole-plate 14 is at the position $14_A$ When the scanning pinhole-plate 14 moves along the arrows 20 to produce the linear scanning, the scanning pinhole-plate 14 produces via the pinhole 0 at the scanning position $14_B$, the solid forward scanning-angle 38 of the pixel 35 having the same primary axis $0_A$ of the solid scanning angle 36. It should be noted that in all the figures where the 20 are shown, these arrows are oriented normal to imaging plane 10.

From FIG. 6 the following can be noted:
1. During the scanning of the plate 14, the primary axis $0_A$, which is normal to imaging plane 10 and parallel to the scanning direction of plate 14, does not change orientation during the scan and thus, the solid scanning-angles 36 and 38 do not change orientation during the scan of the plate 14.

2. The solid-scanning-angle 36 is smaller than the solid scanning angle 38 and is completely included in the angle 36. The scanning angle 36 is the scanning angle when the 14 is at the scan position $14_A$ and is also included in the scanning angle 38 when the plate 14 is at the scanning position $14_B$. Thus, the scanning angle 36 appears once as the isolated angle in the scan position $14_A$ and also appears a second time, in the scan position, $14_B$ as being included in the scanning angle 38, thereby representing the redundancy information included in the scanning angle 38.

3. FIG. 6 is a specific case related only to pinhole 0. In this case, the variable collimation includes only the change in the viewing angles of the scanning angles 36 and 38 without changing the orientation of the corresponding primary axis 18 which remains normal to the imaging plane 10 over the scan of the plate 14.

Thus, when using pinholes, such as the pinhole 0, which produces scanning viewing angles, such as the angles 36 and 38 having primary axis, such as $0_A$ that is normal to imaging planes with the imaging plane 10 also parallel to the scan direction, such as the scan along the arrows 20, the data acquired for the imaging includes a significant amount of redundancy data that may produce poor image reconstruction that may also suffer from artifacts. For example, a scan that is performed in a way that each scanning angle includes all the previous scanning angles produces a large amount of redundant information, which may be avoided or reduced in accordance with various embodiments.

Figure 7:
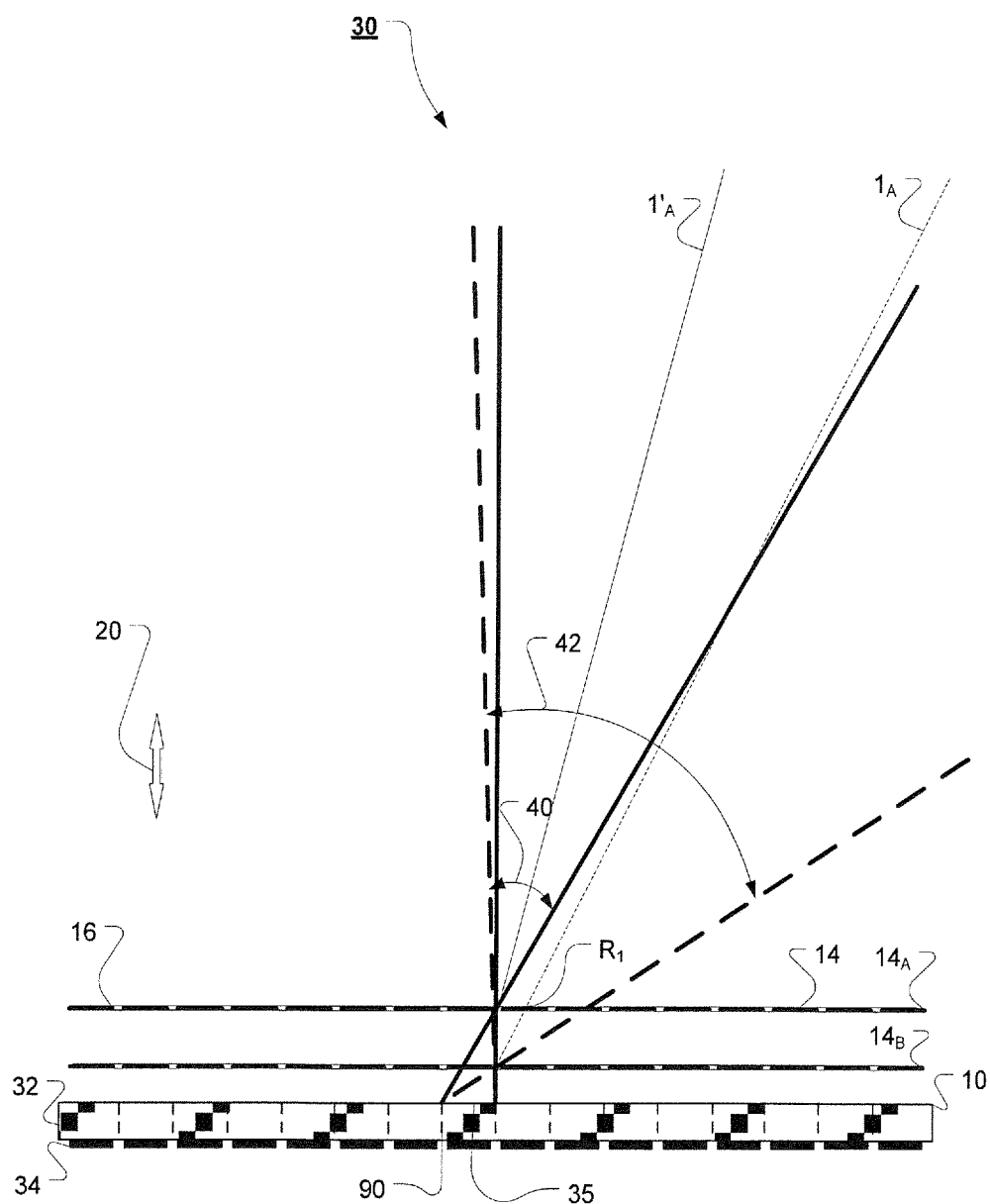

FIG. 7 illustrates a schematic side-view of the scanning unit 30 in a configuration when the forward viewing solid scanning-angles, such as the angles 36 and 38 of FIG. 6 are blocked to avoid the redundant information produced by such forward angles and having the primary axis $0_A$ normal to imaging plane 10 and parallel to the scan direction 20 of the pinhole-plate 14. Accordingly, the pinhole 0 of FIGS. 1-5 and 6 does not exist in the scanning unit 30 of FIG. 7. When the pinhole-plate 14 is at the position $14_A$, the pixel 35 of the pixels 34 in the imaging plane 10 of the detector 32 views the imaged object (not shown) with the scanning viewing angle 40 via the pinhole $R_1$, which is displaced to the right of the center of the pixels 35. When the plate 14 moves along the arrows 20 to produce the linear scan, the pinhole-plate 14 moves to the position $14_B$ where the pinhole $R_1$ produces for the pixels 35, the viewing scanning-angle 42.

The displacement of the pinhole $R_1$, which is displaced to the right of the center of the pixels 35, relative to the center of the pixels 35 produces non-forward scanning angles 40 and 42 having primary axes $1'_A$ and $1_A$, respectively, that are not normal to the imaging plane 10 and not parallel to the scan direction of the plate 14 along arrows 20. The displacement of the pinhole $R_1$ relative to the center of the pixel 35 creates inclined primary axes $1'_A$ and $1_A$ to ensure that the linear scanning of the plate 14 along the arrows 20 will produce the non-forward angular scan of the scanning angles 40 and 42.

While FIG. 7 illustrates and is described in connection with the pixel 35, each of the pixels 34 has a corresponding pinhole, such as the pinholes $R \ldots R_n$ and $L_1 \ldots L_m$ (see FIGS. 1-5) that do not include the pinhole 0 and are distributed symmetrically with respect to the pixels 35 in the illustrated. The array of pinholes 16 and the array of pixels 34 have the same two dimensional pitch λ and are displaced with respect to each other in two dimensions by a distance λ/2 that is equal to half of their pitch in various embodiments. In this configuration, the projections of the pinholes 16 onto the imaging plane 10 are aligned with the lines 90, which are the borderlines between adjacent pixels 34. The scanning-angle 42 corresponding to the scan position $14_B$ of the plate 14 is rotated relative to the scanning-angle 40 corresponding to the scan position $14_A$ of the plate 14. Since the plate 14 is much closer to the pixels 35 at the scan position $14_B$ than at the position $14_A$, the collimation is much wider than the collimation of the scanning-angle 40. Thus, even though the scanning angle 42 is rotated relative to the scanning angle 40, the collimation of the angle 42 that is much wider than that of the angle 40 causes the angle 42 to include the angle 40 in a way that may produce redundant information in the data acquired from the imaged object during the scan of the plate 14.

FIG. 7, unlike FIG. 6 is a case related to the pinholes 16 excluding pinholes 0. In this case, the variable collimation includes both the change in the collimation of the viewing angles of the scanning angles, such as the angles 40 and 42 and the change in the orientation of the primary axis 18, such as the axes $1'_A$ and $1_A$, which are inclined with respect to the normal of the imaging plane 10 over the scan of plate 14.

Figure 8:
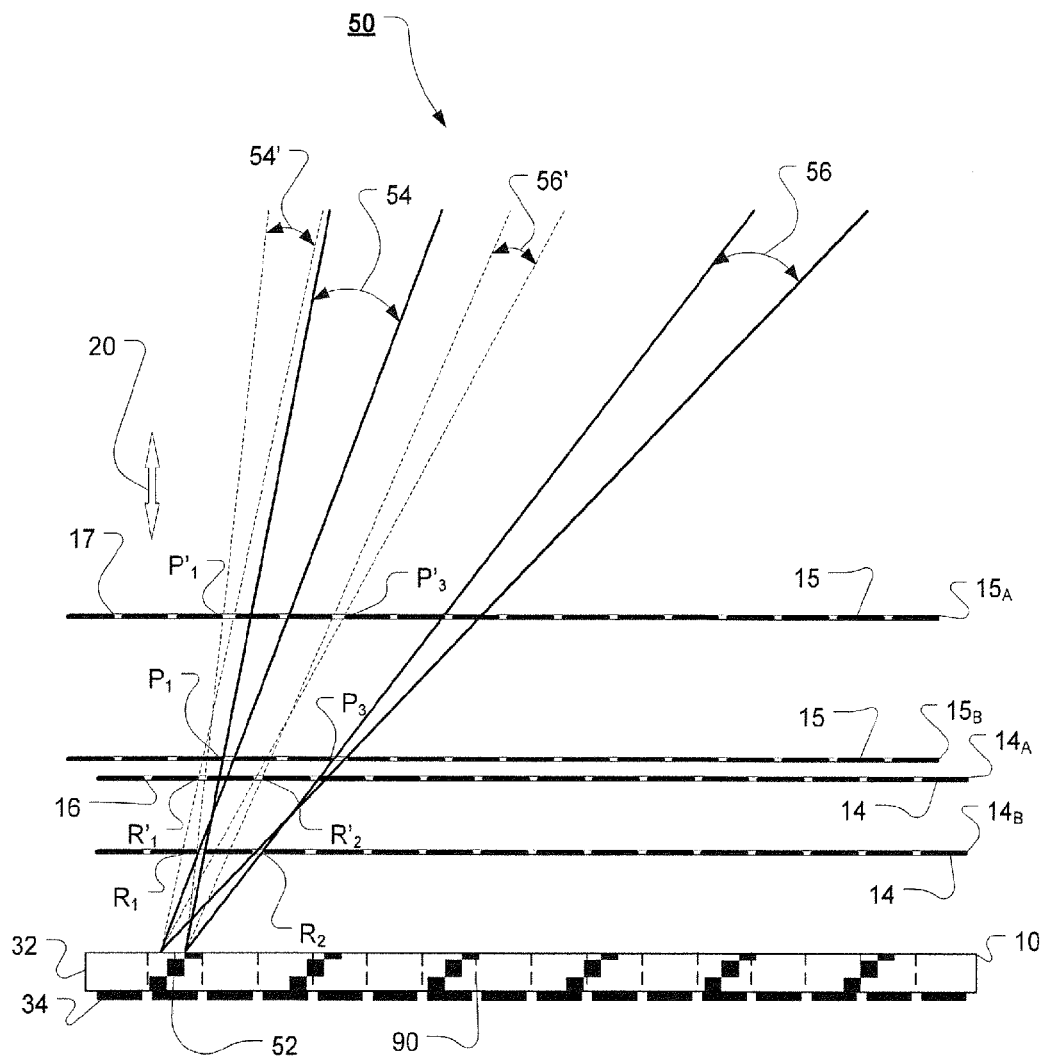

FIG. 8 schematically illustrates a side view of the scanning unit 50 configured to produce rotating non-forward scanning-angles for creating angular scanning. The scanning angles of the unit 50 rotate similar to the scanning angles of the unit 30 of FIG. 2b. In addition to the rotation of the scanning angles of the unit 30, the scanning angles of the scanning unit 50 of FIG. 8 also have collimation controls. These controls are used to avoid or reduce the likelihood that the rotated scanning angle at a certain angular-scan position, in spite of the rotation and due to collimation broadening, includes a significant fraction of the previous scanning angle while being in a previous rotating position of the angular scan.

FIG. 8 is a schematic illustration of the scanning unit 50 including the pixelated detector 32 having the pixels 34 forming the imaging plane 10. While the pixelated detector 32 is illustrated by FIGS. 6, 7 and 8 with the anodes of the pixels 34 facing down and the imaging plane 10 on the upper cathode surface of the detector 32, the detector 32 may be used in different configurations, such as when the anodes of the pixels 34 are facing up to coincide with the imaging plane 10. In this configuration, the cathode plan of the detector 32 is facing up, as illustrated by FIGS. 6 and 7 and unlike FIGS. 9, 21-23 and 26 in which the cathode is facing down. The scanning unit 50 includes two scanning pinhole-plates 14 and 15. The pinhole-plate 14 of the scanning unit 50 operates similar to the operation of the pinhole-plate 14 of the scanning unit 30 as illustrated by FIG. 7 and the pinhole-plate 15 of the scanning unit 50 operates similar to the operation of the pinhole-plate 14 of the scanning unit 30 as illustrated by FIGS. 1-6 and as described in more detail herein.

The pinhole-plate 15 is not included in the scanning unit 30 and is added to the scanning unit 50 for controlling the collimation of the scanning angles produced by the pinhole-plate 14. The collimation control of the pinhole-plate 15 in various embodiments is determined by the size of the pinholes 17 in the plate 15, the distance between the plates 14 and 15 and the relative position between the plates 14 and 15.

In an initial scan position of the scanning unit 50, the plates 14 and 15 are located at the scan positions $14_A$ and $15_A$, respectively. In this initial scan position, the solid scanning-angles 54' and 56' are the viewing angles via which the imaged object (not shown) is observed by the pixel 52. The solid scanning-angle 54' is produced by the pinhole $P'_1$ of the pinholes 17 in the plate 15 and the pinhole $R'_1$ of the pinholes 16 in the plate 14. Similarly, the solid scanning-angle 56', which is also the viewing angle via which the imaged object (not shown) is observed by the pixels 52, is produced by the pinhole P'₃ of the pinholes 17 in the plate 15 and the pinhole R'₂ of the pinholes 16 in the plate 14.

During a scan, both the plates 14 and 15 change scan positions and move in a direction along the arrows 20. When the plates 14 and 15 move during the scan into the scan positions 14$_B$ and 15B, respectively, the scanning angles 54 and 56 are produced. The scanning angle 54 is rotated to the scanning angle 54' corresponding to the positions 14$_A$ and 15$_A$, of the plates 14 and 15, respectively, which produce an angular scan, due and in response to the linear scan of the plates 14 and 15, for moving from an initial scan position as the angle 54' to appear, after the rotation of the angular scan, as the scanning angle 54 corresponding to the scan positions 14$_B$ and 15$_B$, of the plates 14 and 15, respectively.

The solid scanning-angle 54 is produced by the pinhole P₁ of the pinholes 17 in the plate 15 and the pinhole R₁ of the pinholes 16 in the plate 14. Similarly, the solid scanning-angle 56, which is also the viewing angle via which the imaged object (not shown) is observed by the pixels 52, is produced by the pinhole P₃ of pinholes the 17 in the plate 15 and the pinhole R₂ of the pinholes 16 in the plate 14 when the plates 14 and 15 are in the scan positions 14$_B$ and 15$_B$, respectively.

From FIG. 8, it can be seen that the scanning angles 54 and 56 do not contain the scanning angles 54' and 56' which are the scanning angles 54 and 56 in the previous angular scan position. In addition, it can be seen from FIG. 8 that the scanning angles 54' and 56', corresponding to the initial scanning position of the scanning unit 50, do not overlap each other. Similarly, the scanning angles 54 and 56, corresponding to another scanning position of the scanning unit 50, do not overlap each other as well. Accordingly, the scanning unit 50 is capable of producing angular scanning while the redundant information acquired during the scan is reduced or substantially reduced in comparison to the scan of the scanning unit 30. Using the scanning unit 50 with the collimation control of the 15 limits the collimation broadening of the scanning angles produced by the plate 14 while the angular scan of the scanning angles is performed.

The scanning plate 15 added to scanning plate 14 in FIG. 8 produces the scan together with the plate 14 by moving along the arrows 20. The array of pinholes 16, the array of pinholes 17 and the array of pixels 34 all have the same two-dimensional pitch in the illustrated embodiment. As described above, the array of pinholes 16 is displaced with respect to the array of pixels 34 by a distance λ/2 that is equal to half of the pitch in a way that the projections of the pinholes 16 onto the imaging plane 10 are aligned with the lines 90, which are the border-lines between adjacent pixels 34. While the two-dimensional array of pinholes 17 of the plate 15 still has the same pitch as the array of pinholes 16, the projections of the pinholes 17 onto the imaging plane 10 are aligned with the centers of the pixels 34.

FIG. 9 schematically illustrates the side view of a scanning unit 70, which is similar to scanning unit 50. In the scanning unit 70, the variable collimation includes both, controlling the collimation of the viewing angles of the scanning angles and changing the orientation of the scanning angles.

FIGS. 9 and 10 are schematic side and top views of the scanning unit 70, respectively. FIGS. 9 and 10 illustrate that each pixel 34 in the imaging plane 10 has multiple non-forward scanning-angles resulting in the high-sensitivity scanning unit 70. Accordingly, each pixel 34 receives radiation from an imaged object emitting radiation along multiple radiation paths from the object to the radiation detector 32 via the pinholes 16 and 17 of the plates 14 and 15, respectively. Even though each pixel 34 has multiple scanning angles, for the clarity of the drawings, only a few pixels, such as the pixels 98, 52 and 120 are shown with corresponding scanning angles and even these pixels are shown with only a few scanning angles.

FIG. 9 shows the pixelated detector 32 having the pixels 34 arranged in a matrix form inside the imaging plane 10. The scanning plates 14 and 15, capable of bidirectional movement in a direction normal to the imaging plane 10 along the arrows 20, include two dimensional arrays of the pinholes 16 and 17 respectively. The surface 84 of the plate 14 is the radiation blocking surface of plate 14.

In some embodiments, the two dimensional array of the pinholes 16 of the plate 14 are registered with the two dimensional array of pixels 34 of the detector 32 such that the pinholes 16 are aligned off center with respect to the center of pixels 34. In the illustrated embodiment, the array of the pinholes 16 has the same pitch λ as the pitch of array of the pixels 34 (shown as the distance λ between the lines 86 and 90) and corresponding projections on the imaging plane 10 are aligned to be positioned on the borders between adjacent pixels 34 (shown by the points 92 and 94). The relative position between the pinholes 16 and the pixels 34 is illustrated by the pinholes L'$_i$ and L'$_j$ and the lines 86 and 90. The lines 86 and 90 passing through the pinholes L'$_i$, and L'$_j$ of the array of pinholes 16 of the plate 14 intersect with the imaging plane 10 at points 92 and 94, which are the projections of the pinholes L'$_i$, and L'$_j$ on the imaging plane 10 and are located in the borders between adjacent pixels 96, 98, and 100 of the pixels 34. It can be seen that for avoiding or reducing the likelihood of redundant information similar to the redundant information produced during the scan by scanning unit 30 of FIGS. 1-6, the plate 14 of the scan unit 70 does not include any pinholes 0 above any of the pixels 34. All the projections of the pinholes 16 of the plate 14 on the imaging plane 10 are displaced by a distance λ/2 from the centers of the pixels 34 (as shown by the lines 86 and 90) and located in the borders between adjacent pixels 96, 98 and 100 of pixels 34 (as shown by the lines 86 and 90 and intersection points 92 and 94 with the imaging plane 10).

The two dimensional array of pinholes 17 of the plate 15 are registered with the two dimensional array of pixels 34 of the detector 32 such that the pinholes 17 are aligned to the center of the pixels 34. The array of pinholes 17 has the same pitch λ as the pitch of array of pixels 34 (shown as the distance λ between the lines 86 and 90) and corresponding projections on the imaging plane 10 are aligned with the centers of the pixels 34 (shown by the point 102). The relative position between the pinholes 17 and the pixels 34 is illustrated by the pinhole Q'$_k$ and the line 88. The line 88 passing through the pinhole Q'$_k$ of the array of pinholes 17 of the plate 15 intersects with the imaging plane 10 at points 102, which is the projection of the pinhole Q'$_k$ on the imaging plane 10 and is located in the center of the pixel 98 of the pixels 34. It can be seen that for avoiding or reducing the likelihood of redundant information similar to the redundant information produced during the scan by scanning unit 30 of FIGS. 1-6, the plate 14 of the scan unit 70 blocks the radiation path between the pixels 34 and the pinholes 0 of the array of pinholes 17 of the plate 15 located above the centers of the pixels 34, such as the pinhole 0 above the center of the pixel 52. All the projections of the pinholes 17 of the plate 15 on imaging plane 10 are aligned with the centers of the pixels 34 and displaced by a distance λ/2 from the borders of the pixels 34 (as shown by the lines 88 and 90) and located in the centers of the pixels 34 (as shown by the line 88, intersection point 102 with the imaging plane 10 and the pixel 98).

As described above, each pixel 34 of the 32 has multiple scanning angles. For the clarity of the drawing of FIG. 9, only a few of the pixels 34 are shown with only a few corresponding scanning angles. For example, the pixel 96 is shown with corresponding scanning angles 104 and 106 that scan clockwise and are illustrated by bold lines. The angles 104 and 106 pass through the pinholes 17 and 16 of the scanning plates 14 and 15, respectively. The pixel 52 is shown with part of corresponding scanning angles 72 and 74 that scan clockwise and are illustrated by bold lines. The scanning angles 76 and 78 of the pixels 52 that scan counterclockwise are illustrated by broken lines. Similarly, the pixel 120 is shown with part of corresponding scanning angles 108 and 110 that scan clockwise and are illustrated by bold lines. The scanning angles 112 and 114 of the pixel 120 that scan counterclockwise are illustrated by broken lines. The pixel 122 is illustrated as having the scanning angles 116 and 118 that scan counterclockwise and are shown by broken lines. It should be noted that the scan orientations, clockwise or counterclockwise, of the viewing angles described above are for when the plate 14 moves towards the detector 32.

All of the scanning angles shown in FIG. 9 pass through the pinholes 17 and 16 of the scanning plates 14 and 15, respectively. For example, the scanning angle 72 passes via the pinholes $R'_2$ and $P'_3$ of the scanning plates 14 and 15, respectively. The scanning angle 74 passes via the pinholes $R'_1$ and $P'_1$ of the scanning plates 14 and 15, respectively. The scanning angle 76 passes via the pinholes $L'_1$ and $Q'_1$ of the scanning plates 14 and 15, respectively and the scanning angle 78 passes via the pinholes $L'_2$ and $Q'_3$ of the scanning plates 14 and 15, respectively.

In operation, the scanning angles of the unit 70, such as the scanning angles 72, 74, 76 and 78, change orientation and collimation (solid viewing angles) in response to the scan position of the unit 70, i.e. the relative positions between the plates 14 and 15 and the imaging plane 10.

The line 124 passing via the pinholes $R'_2$ and $P'_{13}$ of the scanning plates 14 and 15, respectively, represents one of many possible radiation paths, which are not shown in the drawing of FIG. 9, along which the scanning angles of the pixels 34 exist. The pinholes 17 of the plate 15 are located at distances S from the line 88 that are equal to:

$$S = I \cdot \lambda \qquad \text{Eq (2)}$$

When 1 is an integer number 0, 1, 2, 3 . . . .

The pinholes 16 of the plate 14 are located at distances S from the line 88 that are equal to:

$$S = J \cdot \lambda + \lambda/2 \qquad \text{Eq (3)}$$

When J is an integer number 0, 1, 2, 3 . . . .

The distance between the plates 14 and 15 is equal to the distance between the plate 14 and the imaging plane 10. Thus, a scanning angle that starts at the 34 and passes through the pinholes 16 and 17 of the plates 14 and 15 should pass via the pinhole 17 with a displacement S from the line 88 that is twice the displacement s of the pinhole 16 from the line 88. These relations are maintained as long as the distance between the plates 14 and 15 is equal to the distance between the plate 14 and the imaging plane 10.

According to these relations and equations (2) and (3), while scanning angles starting at the pixel 98 pass through the pinholes 17 of the plate 15 that are positioned in odd places relative to the line 88 (1=1, 3, 5 . . . ), the same scanning angles would pass via the pinholes 16 of the plate 14 that are positioned continuously in positions J=0, 1, 2, 3, 4 . . . . In other words, for satisfying the requirement that distance S of Eq (2) is twice the distance s of Eq (3), the index I of Eq (2) and the index J of Eq (3) should satisfy:

$$I = 2 \cdot J + 1 \qquad \text{Eq (3a)}$$

Figure 17:
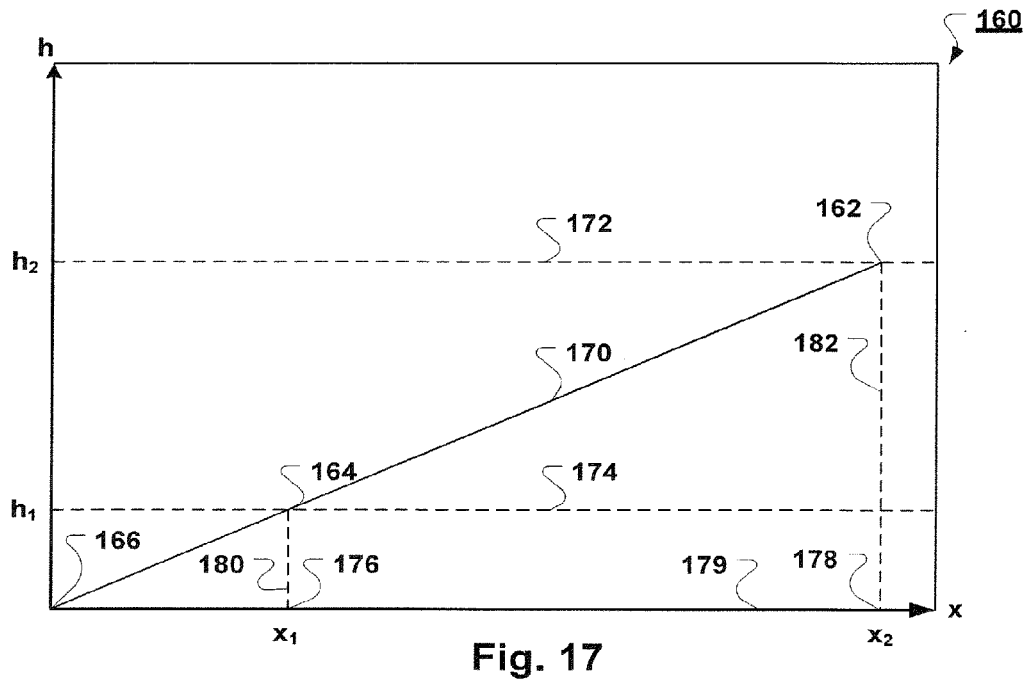
FIGS. 17-20 schematically illustrate the relative positions between the scanning plates of the units illustrated by FIGS. 8 and 9 showing the conditions for producing continuous and step-by-step scans.
Figure 18:
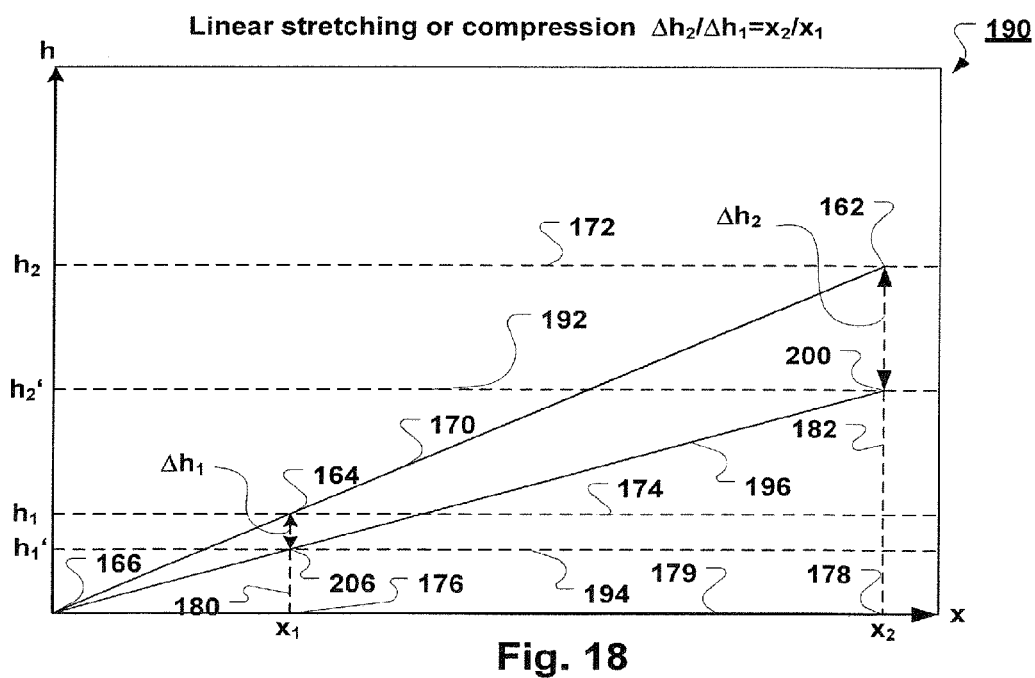

The relative scan position of the plates 14 and 15, the imaging plane 10, the pinholes 16 and 17 of the plates 14 and 15, respectively, during a scan similar to the scan of the scanning unit 70 is illustrated by FIGS. 17 and 18 and is described in more detail in connection with these figures.

FIG. 10 is a schematic top-view illustration of the scanning unit 70 shown in FIG. 9. The top-view illustrates the plate 15 on top of the plate 14 in a way that hidden pinholes/slots 16 of the plate 14 located underneath plate 15 are illustrated by broken lines. The square pinholes of the pinhole array 17 of plate 15 are filled with hatched lines to indicate the surface of the plate 14 viewed via the pinholes 17 of plate 15. The squares 84 illustrated by the broken lines are the radiation blocking surfaces of the plate 14 that are hidden under the plate 15. The square pinholes 17 are aligned with the centers of pixels 34 of the detector 32 of FIG. 9 and are hidden under surfaces the 84 of the plate 14.

FIG. 10 illustrates the top view of the intersection points 138 between the plane of the plate 15 of FIG. 9 and the primary axes, similar to the primary axes 18 of FIGS. 1-5, of the scanning angles viewed by the pixel 52 of the pixels 34 located under the pinhole 0 of the plate 15. It should be apparent that each pixel 34 in the pixelated detector 32 of FIG. 9, may have a corresponding coordinate system in which each pinhole 17 of the plate 15 located above each pixel 34 is marked as the pinhole 0 corresponding to the coordinate system of the respective pixel 34. It can be seen that the scanning angles of the pixel 52 produce a two-dimensional scan while the primary axes passing through the points 138 arranges along the square frames 126, 128 and the lines 130, 132, 134 and 136 illustrated by broken lines. The lines 130 and 136 are part of a large square frame, only part of which is shown in FIG. 10. The lines 132 and 134 are part of two other square frames, with only parts thereof shown in FIG. 10.

The pinholes $P'_1$ and $Q'_1$ of the plate 15 through which the scanning angles 74 and 76 pass, are located in the square frame 126 indicating one scanning dimension out of the two dimensional scan of FIG. 9. Similarly, the pinholes $P'_3$ and $Q'_3$ of the plate 15 through which the scanning angles 72 and 78 of FIG. 9 pass, are located in the square frame 128 indicating one scanning dimension out of the two dimensional scan of FIG. 9.

The lines 86, 88 and 90 are common to FIGS. 9 and 10 and show the relative position between the plates 14 and 15 and illustrate the pitch size 2 of the pinholes 16, 17 and the pixels 34. The lines 86, 88 and 90 also show the displacement by an amount of λ/2 between the pinholes (slits) 16 and the pinholes 17 of the plates 14 and 15, respectively. Additionally, these lines show the registration between the pinholes (slits) 16 of the plate 14 and the borders between the pixels 34 and the registration between the pinholes 17 of the plate 15 and the centers of the pixels 34, respectively.

Figure 14:
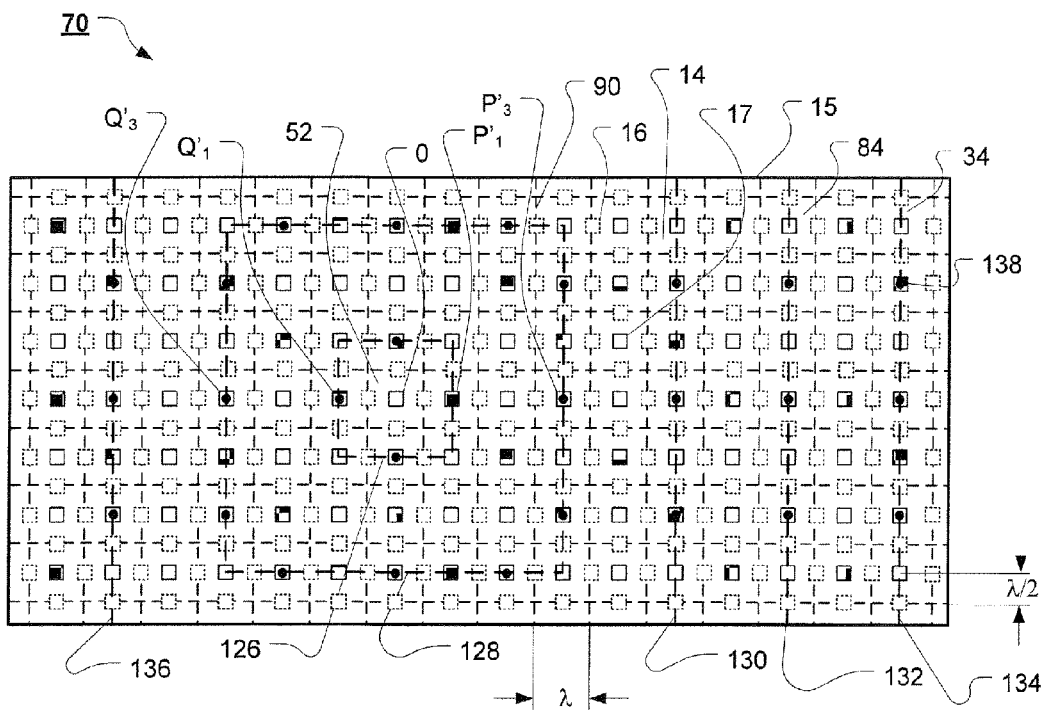
FIGS. 14-16 are schematic top-view illustrations of another embodiment of the radiation-blocking scanning-plates of the scanning units show in FIGS. 8 and 9.
Figure 15:
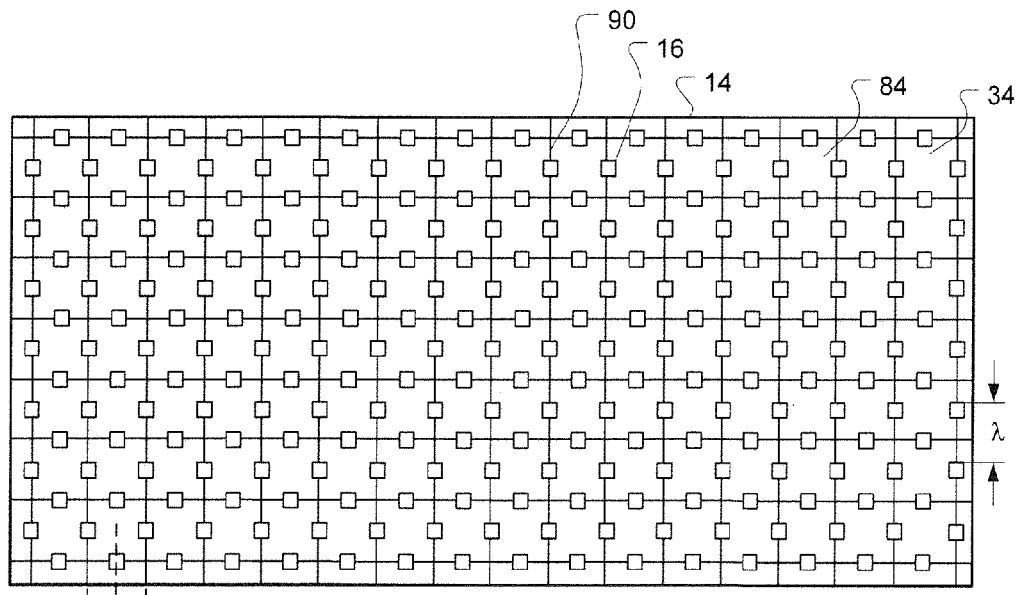
Figure 16:
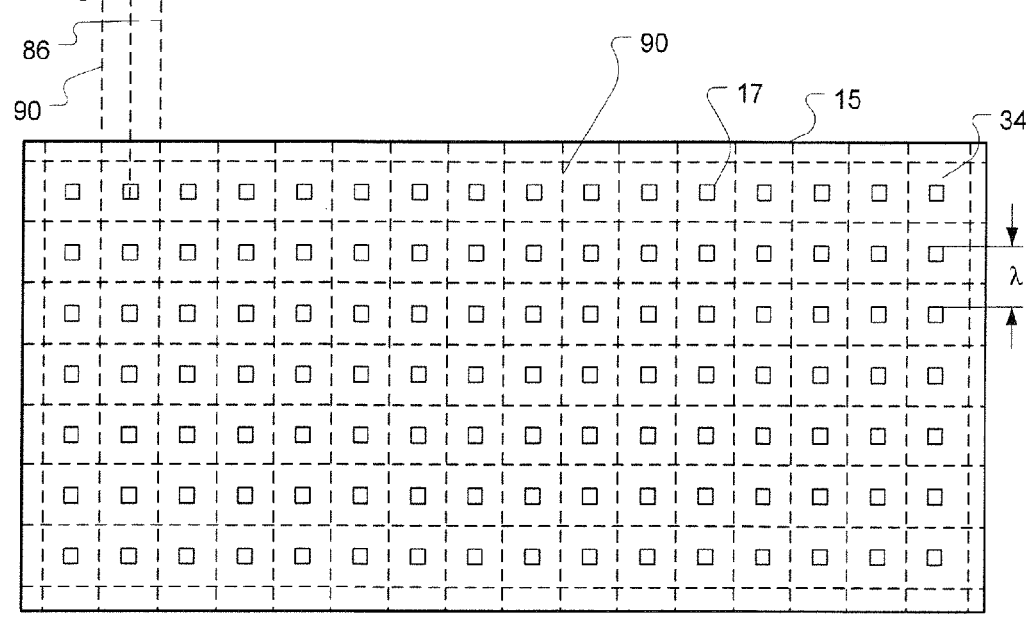

It should be noted that the openings 16 in the plate 14 are shown as pinholes in the side view illustration of FIG. 9 and as can be seen are slits between the squares 84 as shown in FIG. 10. The configuration of the plate 14 is shown in detail in FIGS. 11-12. The additional configuration of the plate 14 is shown in FIGS. 14-16. FIG. 14 shows the plate 15 above the plate 14 similar to the top view illustration of FIG. 10. FIGS. 15 and 16 illustrate the plates 14 and 15 as standalone scanning plates, respectively.

Figure 11:
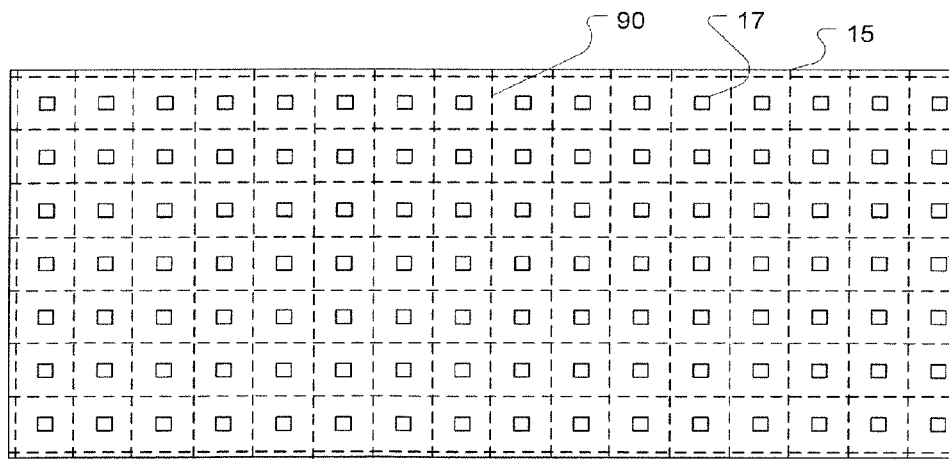
Figure 12:
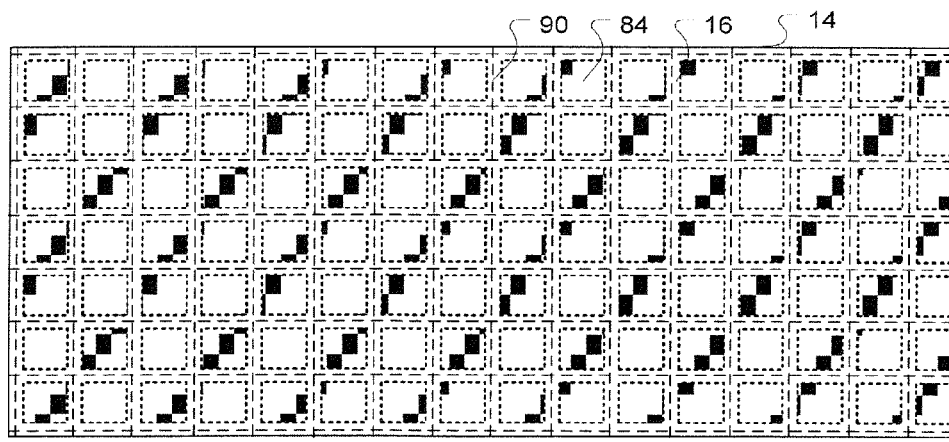
Figure 13:
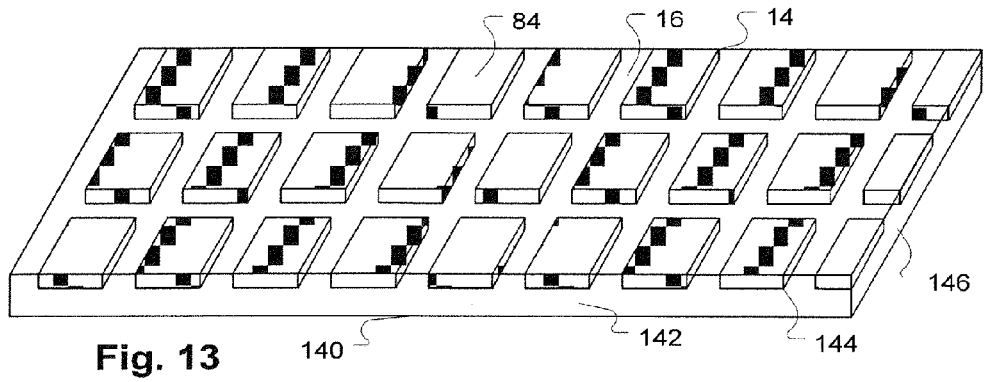

For better illustration of the scanning plates 14 and 15, FIGS. 11, 12 and 13 show a schematic top view of the plate 15, a schematic top view of the plate 14 and a perspective view of part of the plate 14, respectively. The plates 14 and 15 in one embodiment are made of high absorption materials such as Lead (Pb) and Tungsten (W) and having thicknesses designed to block the ionizing radiation emitted from the imaged object toward the radiation detector 32 of FIG. 9 (not shown).

FIG. 11 schematically shows the plate 15 and array of square pinholes 17. The broken lines 90 indicate the borders between the pixels 34 (not shown) of the detector 32 (not shown) of FIG. 9. It can be seen that the pinholes 17 are aligned to the centers of the pixels 34. Additionally, and as can be seen from FIGS. 9, 10, 12, 14, 15 and 16, the pinhole arrays 16 and 17 and pixels 34 have the same two-dimensional pitch that is equal to λ.

FIG. 12 schematically illustrates the scanning plate 14 including square radiation-blocking surfaces 84 that are centered above the pixels 34 of FIG. 9 (not shown) with borders 90 illustrated by the broken lines 90. As previously described, the radiation-blocking surfaces 84 prevent radiation passing through pinholes 0 of the pinholes 17 of the plate 15 in the scanning unit 70 of FIG. 9 from arriving to the pixels 34. The gaps between the radiation-blocking surfaces 84 are the slits 16 appearing as the pinholes 16 in the side-view illustration of FIG. 9.

FIG. 13 is a schematic perspective view of the plate 14 demonstrating how the surfaces 84 that are isolated from each other, by the gaps of the slits 16, are maintained on the same plan in an array form. As can be seen from FIG. 13, the plate 14 includes a supporting substrate 140 that is substantially transparent to the ionizing radiation used for the imaging by the scanning unit 70 of FIG. 9. The substrate 140 includes cavities 144 inside which the radiation-blocking material from which the surfaces 84 are made is placed. The gaps between the surfaces 84 are the slits 16 that are transparent to the ionizing radiation used for imaging by scanning unit 70 of FIG. 9. FIG. 13 illustrates, in perspective, only part of the plate 14 that was cut out of a complete plate 14 along sidewalls 142 and 146.

FIG. 14 is a top view illustration of the scanning unit 70 shown in FIG. 9 having an alternative structure of the plate 14 with a corresponding side view illustrated by FIG. 9. The top-view of FIG. 14 illustrates the plate 15 on top of the plate 14 in with the hidden pinholes 16 of the plate 14 located underneath the plate 15 illustrated by broken lines. The plate 14 includes the radiation-blocking surfaces 84. The plate 15 and the arrangement of the pinhole array 17 in this plate and the registration to the centers of the pixels 34 is similar to the plate 15 of FIG. 10. The plate 14 of FIG. 14 having the blocking surface 84 includes the square pinholes 16 that are aligned toward the borders 90 between the pixels 34. While the openings 16 shown as pinholes in the plate 14 in the side-view illustration of FIG. 14, the openings 16 are slits as seen in the top view illustration of FIG. 10, and these openings 16 are square pinholes in the top view illustration of FIG. 14. The configuration of the plate 14 as shown in FIG. 14 can be made from a stand alone plate while the plate 14 of FIG. 10 is made only using a supporting substrate made of material that is transparent to the radiation received by the radiation detector 32. It should be noted that the configuration of the plate 14 according to FIG. 10 has slits 16 with a larger area than the pinholes 16 of FIG. 14, thus, producing a scan with higher sensitivity.

FIG. 14 illustrates a top view of the intersection points 138 between the plane of the plate 15 of FIG. 9 and primary axes, similar to the primary axes 18 of FIGS. 1-5, of the scanning angles viewed by the pixel 52 of the pixels 34 located under pinhole 0 of the plate 15. It can be seen that the scanning angles of the pixel 52 produce a two-dimensional scan while corresponding primary axes passing through the points 138 arranges or aligns along the square frames 126, 128 and the lines 130, 132, 134 and 136 illustrated by the broken lines. The lines 130 and 136 are part of a large square frame with part of this structure shown in FIG. 14. The lines 132 and 134 are part of two other square frames with only portions thereof shown in FIG. 10.

The pinholes P'$_1$ and Q'$_1$ of the plate 15 through which the scanning angles 74 and 76 of FIG. 9 pass are located in the square frame 126 indicating one scanning dimension out of the two dimensional scan of FIG. 9. Similarly, the pinholes P'$_3$ and Q'$_3$ of the plate 15 through which the scanning angles 72 and 78 of FIG. 9 pass are located in the square frame 128 indicating one scanning dimension out of the two dimensional scan of FIG. 9.

The lines 90 show the relative position between the plates 14 and 15 and illustrate the pitch size λ of the pinholes 16, 17 and the pixels 34. The lines 90 also show the displacement by an amount of λ/2 between the pinholes 16 and 17 of the plates 14 and 15, respectively. Additionally, these lines show the registration between the pinholes 16 of the plate 14 and the borders between the pixels 34 and the registration between the pinholes 17 of the plate 15 and the centers of the pixels 34, respectively.

For better illustration of the scanning plates 14 and 15, FIGS. 15 and 16 show a schematic top view of the plates 14 and 15, respectively. The plates 14 and 15 in one embodiment are made of high absorption materials such as Lead (Pb) and Tungsten (W) and have thicknesses designed to block the ionizing radiation emitted from the imaged object toward the radiation detector 32 of FIG. 9 (not shown).

FIG. 15 schematically illustrates the scanning plate 14 including the radiation-blocking surfaces 84 that are centered above the pixels 34 of FIG. 9 (not shown). The lines 90 which are the borders between the pixels 34 (not shown) are illustrated in FIG. 15 by broken lines. The array of the pinholes 16 of the plate 14 are arranged along the lines 90 and have a pitch equal to λ. As previously described, the radiation-blocking surfaces 84 prevent radiation passing through the pinholes 0 of the pinholes 17 of the plate 15 in the scanning unit 70 of FIG. 9 from arriving at the pixels 34.

FIG. 16 schematically shows the plate 15 and array of square pinholes 17. The broken lines 90 indicate the borders between the pixels 34 (not shown) of the detector 32 (not shown) of FIG. 9. It can be seen that the centers of the pinholes 17 are aligned along the line 88, directed to the centers of the pixels 34 and are displaced by a distance λ/2 from the centers of the pinholes 16 of the plate 14 arranged along the lines 86 and 90 as shown in FIG. 15. While FIGS. 8 and 9 are side-view illustrations of the scanning units 50 and 70, respectively, in which the pinholes 16 and 17 and the pixels 34 appear as being arranged in a form of linear arrays, FIGS. 10-13 and 14-16 illustrating top views of the scanning units 50 and 70 clearly show that the pinholes 16 and 17 and the pixels 34 are actually arranged in a form of two dimensional arrays or matrixes. The two dimensional pitch of the pinholes 16 and 17 and the pixels 34 are the same for all pinholes and pixels and is equal to λ.

FIG. 17 is a graph that relates to the positions of the scanning plates 14 and 15 and the imaging plane 10 of FIG. 9. The description of the graph 160 of FIG. 17 and the scanning unit 70 of FIG. 9 refer alternatively to both of the FIGS. 9 and 17. FIG. 17 shows the graph 160 expressing the relationships between the distances $h_1$ (the line 180 in FIG. 17) and $h_2$ (the line 182 in FIG. 17) of the plates 14 (the line 174 in FIG. 17)

and 15 (the line 172 in FIG. 17) from the imaging plane 10 (the line 179 in FIG. 17) of FIG. 9 versus the positions $X_1$ and $X_2$ (marked, in FIG. 17, by reference numerals 176 and 178) of the pinholes 16 (the point 164 in FIG. 17) and 17 (the point 162 in FIG. 17) of the plates 14 and 15, respectively, as measured from the line 88 of FIG. 9. These relationships maintain the mathematical conditions that satisfy the requirement that a straight line, such as the line 124 of FIG. 9 (identified as the line 170 in FIG. 17) representing the radiation path from the imaged object to the detector 32, can pass through the pixels 34 (the point 166 in FIG. 17), the pinhole 16 (the point 164 in FIG. 17) and the pinhole 17 (the point 162 in FIG. 17) of FIG. 9.

As can be seen, the triangle (formed from the points 166, 164, 176) is similar to triangle (formed from the points 166, 162, 178) and thus, the following proportion is satisfied:

$$X_2/X_1 = h_2/h_1 = (166,162)/(166,164) \qquad \text{Eq (4)}$$

when (166,162) and (166,162) are the intervals between the points 166 and 162 and the points 166 and 164, respectively.

FIG. 18 is a graph 190 showing the relationships between the positions of the plates 14 and 15 of FIG. 9 as shown in the graph 160 of FIG. 17 and in additional second scan positions $h'_1$ and $h'_2$ marked as the lines 194 and 192, respectively, of the plates 14 and 15.

The description regarding the graph 190 of FIG. 18 and the scanning unit 70 of FIG. 9 refer alternatively to both of the FIGS. 9 and 18.

The line 196 representing the second orientation of the scanning line 170 passes through the pinholes 16 and 17 marked by the points 206 and 200, respectively. The displacement of the plate 15 from an initial position at the line 172 to a second scan position at the line 192 is equal to the distance between the points 162 and 200 and identified as $\Delta h_2$. Similarly, the displacement of the plate 14 from an initial position at the line 174 to a second scan position at the line 194 is equal to the distance between the points 164 and 206 and is identified as $\Delta h_1$.

The triangle (formed from the points 166, 164, 206) is similar to triangle (formed from the points 166, 162, 200) and thus, the following proportion is satisfied:

$$\Delta h_2/h_1 = (166,162)/(166,164) \qquad \text{Eq (5)}$$

Substituting the value of (166,162)/(166,162) from Eq (4) into Eq (5) results in:

$$X_2/X_1 = \Delta h_2/\Delta h_1 \qquad \text{Eq (6)}$$

wherein Eq (6) gives the formula for the displacements of the scanning plates 14 and 15 that maintains a linear path representing the radiation path from the radiation emitting object to the radiation detector 32 through the pinholes 16 and 17 over the scan range of the plates 14 and 15 in the directions of the arrows 20 as shown in FIG. 9.

Figure 19:
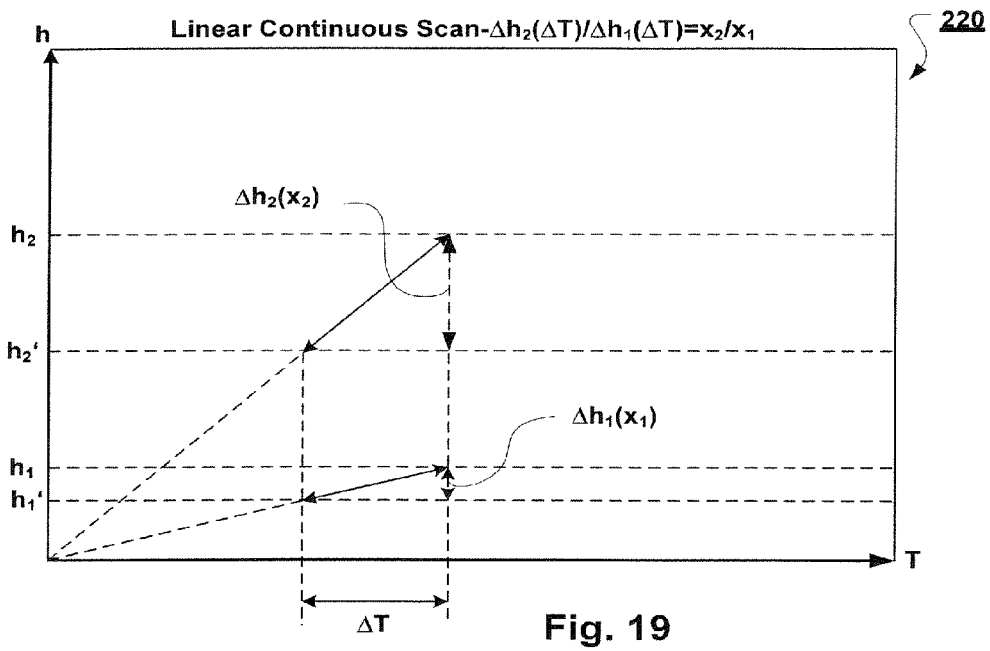
Figure 20:
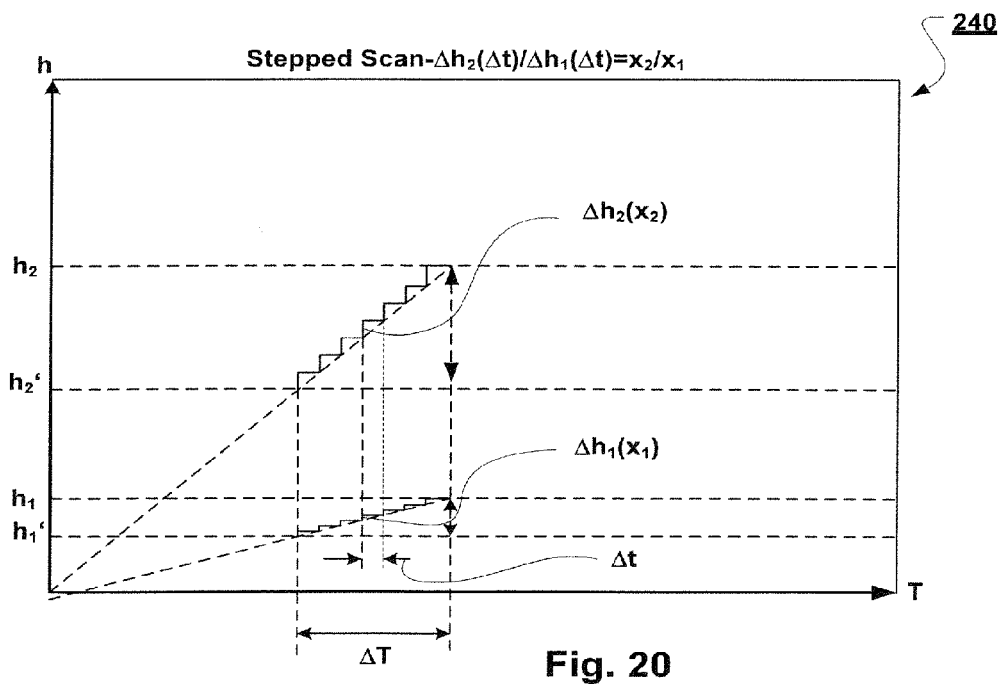

FIGS. 19 and 20 are diagrams 220 and 240 illustrating a continuous scan and a step-by-step scan of the scanning plates 14 and 15 of the scanning unit 70 illustrated by FIG. 9, respectively.

According to FIG. 19, the plates 14 and 15 continuously move distances $\Delta h_1$ and $\Delta h_2$, from a first scanning position where the plates 14 and 15 are located at scan positions $h_1$ and $h_2$, to a second scan position where the plates 14 are 15 are located at scan positions $h'_1$ and $h'_2$, respectively.

As described above, the scan-displacements $\Delta h_1$ and $\Delta h_2$, of the plates 14 and 15 are functions of the locations $X_1$ and $X_2$ of the pinholes 16 and 17 of the plates 14 and 15, respectively. Thus, the displacements $\Delta h_1$ and $\Delta h_2$ are actually $\Delta h_1(X_1)$ and $\Delta h_2(X_2)$, respectively. The diagram 220 of FIG. 19 shows that the plates 14 and 15 move continuously the distances $\Delta h_1(X_1)$ and $\Delta h_2(X_2)$ at a same time $\Delta T$, respectively.

Thus, from Eq (6), the following can be written:

$$X_2/X_1 = \Delta h_1(X_1)/\Delta h_2(X_2) = (\Delta h_1(X_1)/\Delta T)/(\Delta h_2(X_2)/\Delta T) = V_2/V_1 \qquad \text{Eq (7)}$$

where $V_1$ and $V_2$ are the scan velocities of the plates 14 and 15 and are linearly proportional to the positions $X_1$ and $X_2$ of the pinholes 16 and 17, respectively, as measured from a reference position such as the line 88 or the center of any pixel 34 of FIG. 9.

According to FIG. 20, the plates 14 and 15 move step by step distances $\Delta h_1$ and $\Delta h_2$, from a first scanning position where the plates 14 are 15 are located at scan positions $h_1$ and $h_2$, to a second scan position where the plates 14 and 15 are located at scan positions $h'_1$ and $h'_2$, respectively.

As described above, the scan-displacements $\Delta h_1$ and $\Delta h_2$ of the plates 14 and 15 are functions of the locations $X_1$ and $X_2$ of the pinholes 16 and 17 of the plates 14 and 15, respectively. Thus, the displacements $\Delta h_1$ and $\Delta h_2$ are actually $\Delta h_1(X_1)$ and $\Delta h_2(X_2)$, respectively. The diagram 220 of FIG. 19 shows that the plates 14 and 15 move step-by-step distances $\Delta h_1(X_1)$ and $\Delta h_2(X_2)$ while staying at each step position for a same time $\Delta t$, respectively. The time $\Delta t$ is equal to $\Delta T/N$ when N is the number of steps along the scan range.

Thus from Eq (6) the following can be written:

$$X_2/X_1 = \Delta h_1(X_1)/\Delta h_2(X_2) = (\Delta h_1(X_1)/\Delta t)/(\Delta h_2(X_2)/\Delta t) \qquad \text{Eq (8)}$$

Accordingly, the step size in the movement of the scanning plates 14 and 15 are linearly proportional to the positions $X_1$ and $X_2$ of the pinholes 16 and 17, respectively, as measured from a reference position such as the line 88 or the center of any pixel 34 of FIG. 9.

Figure 21:
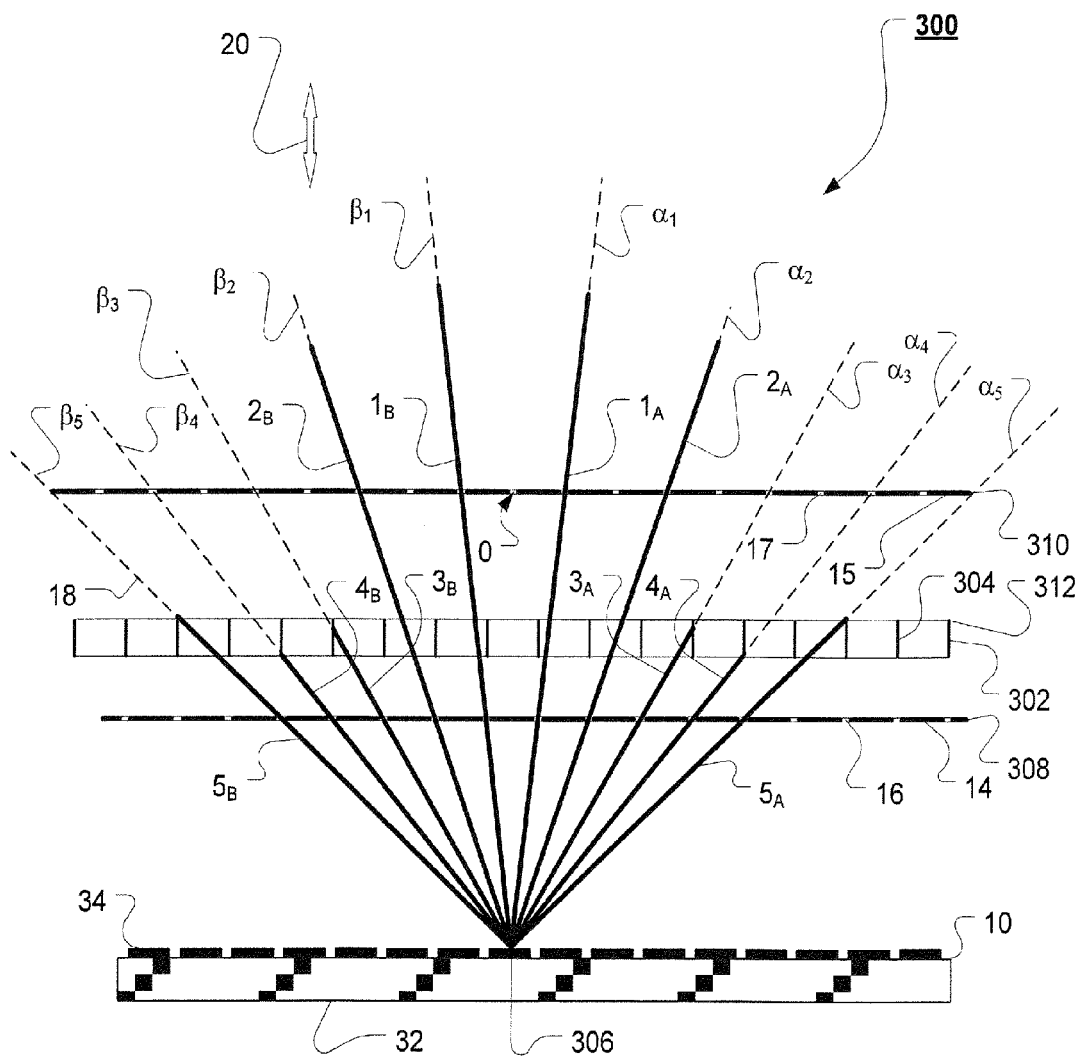
FIGS. 21-23 are schematic illustrations of a scan unit including two scanning plates and partially-blocking scanning-collimator in three scanning positions in accordance with an embodiment.
Figure 22:
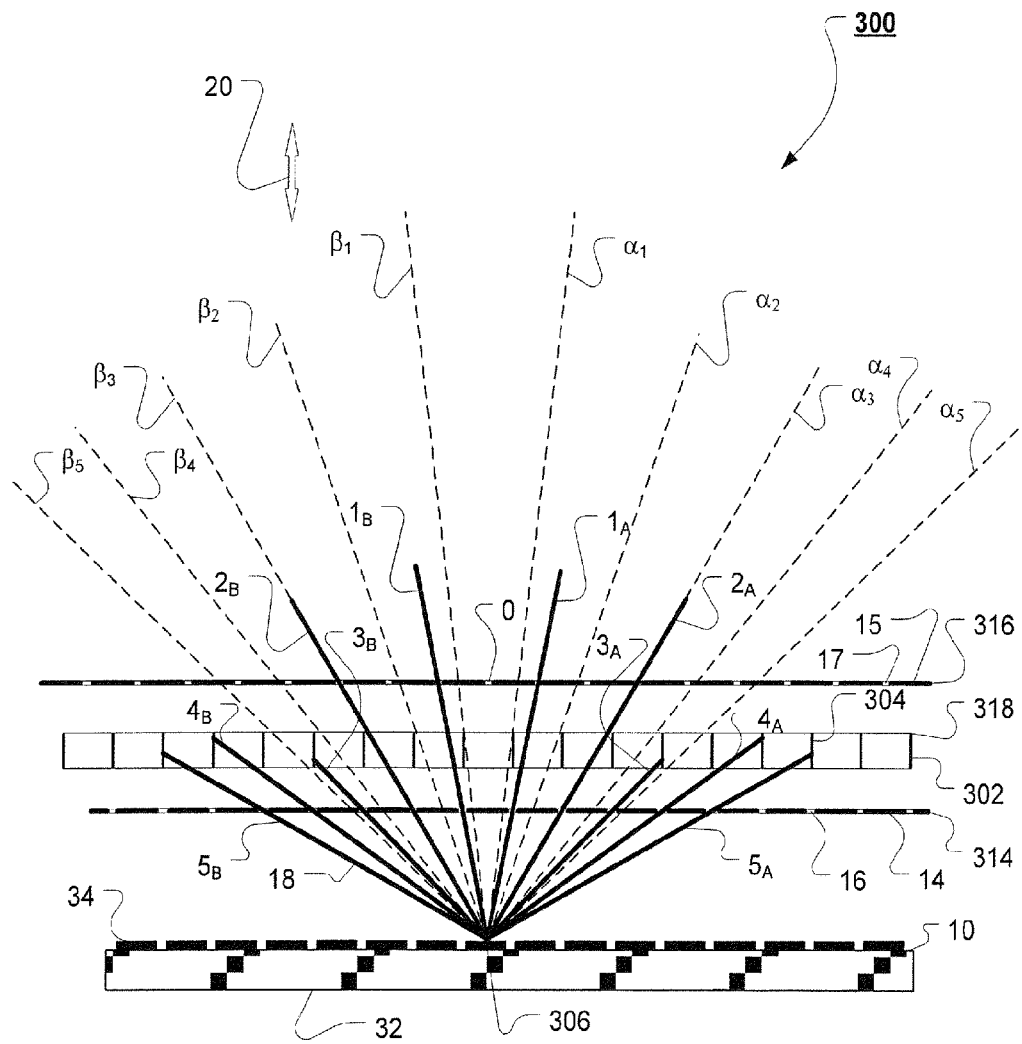
Figure 23:
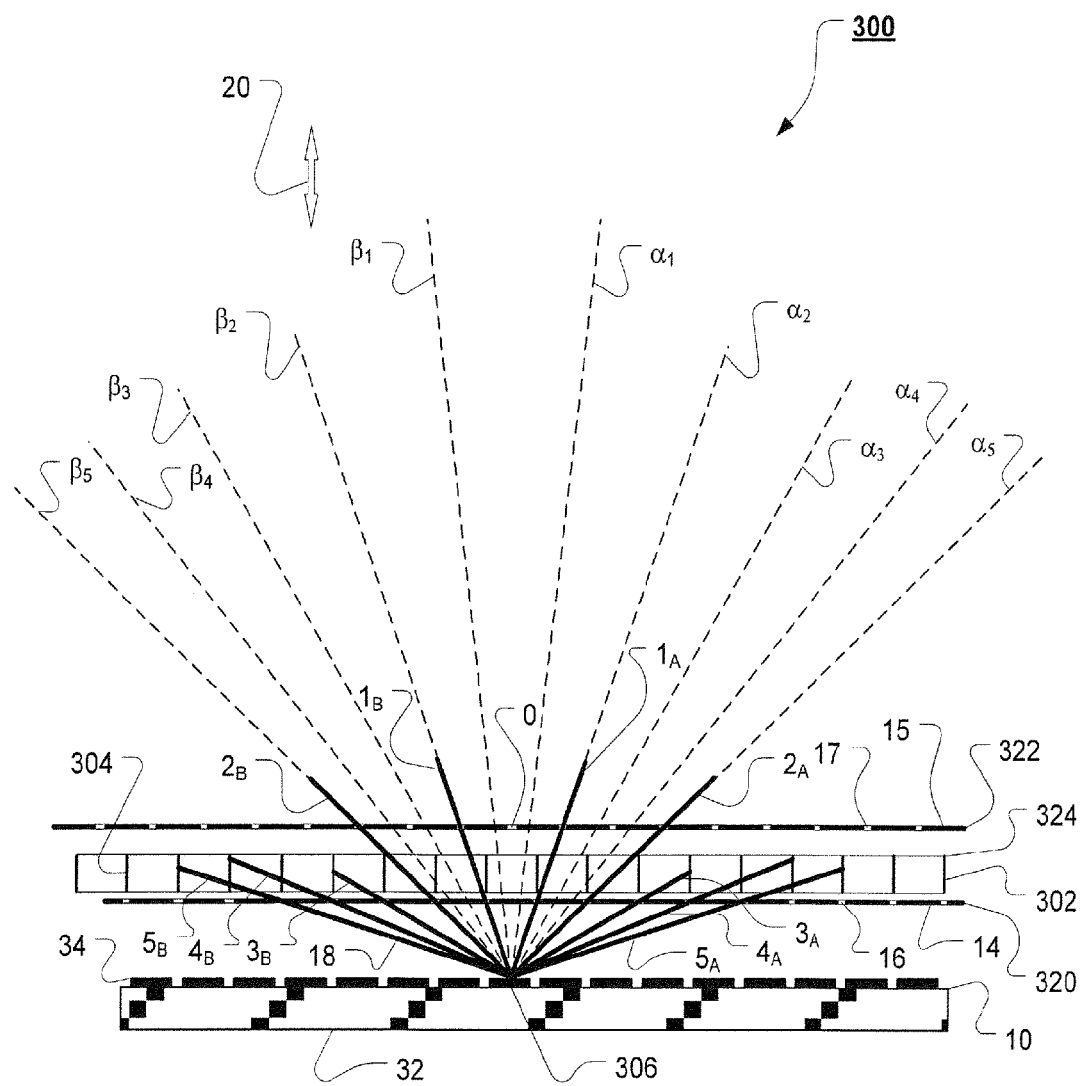

FIGS. 21-23 schematically illustrate a side-view of a scanning unit 300 in three different scan positions. The scanning unit 300, like the scanning unit 70 of FIG. 9 includes the pixelated detector 32 having the pixels 34 arranged in a matrix form in the imaging plane 10 and the scanning plates 14 and 15 located in scan positions 308 and 310 and having the pinhole arrays 16 and 17, respectively.

The scanning unit 300 is similar to the scanning unit 70 of FIG. 9, but includes an additional collimator 302 movable in scan directions along the arrows 20. The scanning angles of a pixel 306 via which the pixel 36 views the imaged object (not shown) are schematically represented by the primary axes 18.

The primary axes 18 start at the pixel 306 and pass through the pinhole arrays 16 and 17 of the scanning plates 14 and 15 toward the imaged object. The scanning angles and corresponding primary axes perform a two dimensional angular scan in response to the bidirectional linear scan (linear movement) of the scanning plates 14 and 15 moving in the directions of the arrows 20 oriented normal to the imaging plane 10. The collimator 302 located in a position 312, includes a septa 304 designed to block all the scanning angles related to the pixel 306 except for the four scanning angles represented by primary axes $1_A$, $2_A$, $1_B$ and $2_B$ of the primary axes 18 representing the first two pairs of scanning angles oriented right and left of pinhole 0 located directly above the center of the pixel 306, respectively. Thus, the collimator 302 acts as a partially blocking collimator that blocks the undesired scanning angles and allows the passage of the desired scanning angles. The collimator 302 in one embodiment may be made of high absorption materials such as Lead (Pb) or Tungsten (W).

The broken lines $\alpha_1$, $\alpha_2$, $\alpha_3$, $\alpha_4$ and $\alpha_5$ identify the position of the primary axes $1_A$, $2_A$, $3_A$, $4_A$ and $5_A$ of the axes 18 when the plates 14 and 15 and the collimator 302 are at the scan positions 308, 310 and 312, respectively. The primary axes $1_A$, $2_A$, $3_A$, $4_A$ and $5_A$ of the axes 18 are directed right of the pinhole 0 and perform a clockwise angular scan, while the plates 14 and 15 linearly move toward the imaging plane 10 and along the arrows 20.

Similarly, the broken lines $\beta_1$, $\beta_2$, $\beta_3$, $\beta_4$ and $\beta_5$ identify the position of the primary axes $1_B$, $2_B$, $3_B$, $4_B$ and $5_B$ of the axes 18 when the plates 14 and 15 and the collimator 302 are at the scan positions 308, 310 and 312, respectively. The primary axes $1_B$, $2_B$, $3_B$, $4_B$ and $5_B$ of the axes 18 are directed left of the pinhole 0 and perform a counterclockwise angular scan while the plates 14 and 15 move toward the imaging plane 10. The clockwise and counter clockwise angular scan of the axes-lines 18 is produced, in response to the linear scan of the plates 14 and 15, by the change of the inclination angles of the lines 18 as measured between the lines 18 and the references lines oriented normal to the imaging plane 10. Additionally, as can be seen from FIGS. 21-23, the inclination angles of the lines 18 depend on the scan position of the plates 14 and 15 in the scanning unit 300.

As described in connection with FIGS. 1-5, the non-repetitive scanning range of the linear scan of plate 14 and the non-repetitive angular scan of the scanning angles represented by the corresponding primary axes 18 increases with the decreasing distance from the pinhole 0 above the pixels 34 to the pinholes 16 and 17 used for the scan and through which primary the axes 18 pass. Accordingly, to provide a large scanning range without acquiring redundant information during the data acquisition derived during the scan of the scanning unit 300 of FIG. 21, the scanning angles that are oriented to pass through the pinholes 16 and 17 located far away from the pinholes 0, which are located above corresponding pixels 34, are blocked by the collimator 302 and only the scanning angles that are oriented close to respective pinholes 0, which are located above corresponding pixels 34, are used for the scan of the scanning unit 300. In the scanning unit 300, as illustrated by side-view, all the scanning angles are illustrated by one dimensional scanning (out of the two dimensional scan of the scanning unit 300) of the pixel 306. In the example of the scanning unit 300, all of the scanning angles represented by the primary axes 18 having indexes higher than 2, which are $3_A$, $4_A$ and $5_A$ right of the pixels 306 and $3_B$, $4_B$ and $5_B$ and left of the pixel 306, are blocked by the collimator 302. The only scanning angles used by the scan of scanning unit 300 are the angles that pass through the collimator 302, in position 312. These scanning angles are the angles with primary axes having indices lower than 2 and are $1_A$ and $2_A$ directed right of the pixels 306 and angles with primary axes $1_B$ and $2_B$ directed left of the pixels 306.

FIG. 22 schematically illustrate the scanning unit 300 in a scan position within the scanning range scanning of the unit 300 that is different from the initial scan position of the scanning unit 300 shown by FIG. 21. In FIG. 22, the plates 14 and 15 and the blocking collimator 302 are at the scan positions 314, 316 and 318, respectively.

While the scanning plates 14 and 15 move from the scan positions 308 and 310 of FIG. 21 to the scan positions 314 and 316 of FIG. 22, respectively, the scanning angles corresponding to the primary axes $1_A$ and $2_A$ perform a clockwise angular scan and the scanning angles with corresponding primary axes $1_B$ and $2_B$ perform a counterclockwise angular scan. The scanning angles corresponding to the primary axes $2_A$ and $2_B$ in the initial scan positions 308 and 310 of the scanning unit 300 of FIG. 21, move from the rotational scanning angles $\alpha_2$ and $\beta_2$ to the rotational scanning angles $\alpha_3$ and $\beta_3$ corresponding to the scan positions 314 and 316 illustrated by FIG. 22, respectively. Similarly, the scanning angles corresponding to the primary axes $1_A$ and $1_B$ in the initial scan positions 308 and 310 of the scanning unit 300 of FIG. 21, move from the rotational scanning angles $\alpha_1$ and $\beta_1$ to the rotational scanning angles oriented between the angles $\alpha_1$ and $\alpha_2$ and $\beta_1$ and $\beta_2$ corresponding to the scan positions 314 and 316 illustrated by FIG. 22, respectively.

At the same time, the blocking-collimator 302 moves from the position 312 of FIG. 21 to the position 318 of FIG. 22. In this position, the collimator 302 still blocks, by the septa 304, the primary axes $3_A$, $4_A$ and $5_A$ oriented right of the pixels 306 and $3_B$, $4_B$ and $5_B$ oriented left of the pixel 306. On the other hand, at this position, the collimator 302 passes the scanning primary axes $1_A$ and $2_A$ directed right of the pixels 306 and $1_B$ and $2_B$ directed left of the pixels 306.

Even though the primary axes $2_A$ and $2_B$, of FIG. 22 are oriented in the directions of the angles $\alpha_3$ and $\beta_3$, which are the previous and initial orientations of s the canning primary axes $3_A$ and $3_B$, in FIG. 21, from which the primary axes $3_A$ and $3_B$ already performed a scan, the primary axes $2_A$ and $2_B$ will not produce redundant information of the acquired information obtained during further scanning from orientations $\alpha_3$ and $\beta_3$. The redundant information is not produced because the scanning primary axes $3_A$ and $3_B$ that were previously in positions $\alpha_3$ and $\beta_3$, and rotated during the scan of the scanning unit 300 from position $\alpha_3$ and $\beta_3$, illustrated by FIG. 21, to positions between $\alpha_4$ and $\alpha_5$ and $\beta_4$ and $\beta_5$, illustrated by FIG. 22, are blocked by the septa 304 of the collimator 302, over the scan range of the scanning unit 300 and thus do not produce any information during the scan of the scanning unit 300.

FIG. 23 schematically illustrate the scanning unit 300 in a final scan position within the scanning range of the scanning unit 300 that is different from the initial scan position of the scanning unit 300 shown by FIG. 21 and also different from the scan position illustrated by FIG. 22. In FIG. 23, the plates 14 and 15 and the blocking collimator 302 are at the scan positions 320, 322 and 324, respectively.

While the scanning plates 14 and 15 move from scan positions 314 and 316 of FIG. 22 to the scan positions 320 and 322 of FIG. 23, respectively, the scanning angles corresponding to the primary axes $1_A$ and $2_A$ continue to perform a clockwise angular scan and the scanning angles with corresponding primary axes $1_B$ and $2_B$ continue to perform a counterclockwise angular scan. The scanning angles corresponding to the primary axes $2_A$ and $2_B$ in the scan position of the scanning unit 300 of FIG. 22 move from the rotational scanning angles $\alpha_3$ and $\beta_3$ to the rotational scanning angles $\alpha_5$ and $\beta_5$ corresponding to the final scan position illustrated by FIG. 23, respectively. Similarly, the scanning angles corresponding to the primary axes $1_A$ and $1_B$ in the intermediate scan position of the scanning unit 300 of FIG. 22 move from the rotational scanning angles oriented between angles $\alpha_1$ and $\alpha_2$ and $\beta_1$ and $\beta_2$ to the rotational scanning angles $\alpha_2$ and $\beta_2$ corresponding to the final scan position illustrated by FIG. 23, respectively.

At the same time, the blocking-collimator 302 moves from the 318 of FIG. 22 to the position 324 of FIG. 23. In this position, the collimator 302 still blocks, by the septa 304, the primary axes $3_A$, $4_A$ and $5_A$ oriented right of the pixels 306 and $3_B$, $4_B$ and $5_B$ oriented left of the pixel 306. On the other hand, when the collimator 302 is in the same position 324, the collimator 302 passes the scanning primary axes $1_A$ and $2_A$ directed to the right of the pixels 306 and $1_B$ and $2_B$ directed to the of the pixels 306.

FIG. 23 illustrates the final scan position, as in this position there is no more space to move the collimator 302. In this position, the collimator 302 almost blocks the scanning primary axes $1_A$, $1_B$, $2_A$ and $2_B$ and there is no space to move the collimator 302 to another scan position that will ensure that during further scan the collimator 302 will not block the scanning primary axes $1_A$, $1_B$, $2_A$ and $2_B$. Additionally, at this final scan position, the primary axes $1_A$ and $1_B$ reach the scanning angles that are oriented in the directions of the angles $\alpha_2$ and $\beta_2$. These angles are the previous and initial orientations of the scanning primary axes $2_A$ and $2_B$, in FIG. 21 and from which the primary axes $2_A$ and $2_B$ already preformed a scan. Thus, a further scan will cause the scanning primary axes $1_A$ and $1_B$ to repeat the scan already performed along the axes $2_A$ and $2_B$ from the angles $\alpha_2$ and $\beta_2$ and onward. Such further scan, if continued beyond the final scan position of FIG. 23, would produce, by scanning the primary axes $1_A$ and $1_B$, undesired redundant information obtained during the scan of the axes $1_A$ and $1_B$ from the angles $\alpha_2$ and $\beta_2$ to the larger scanning angles already scanned by the previous angular scan of the axes $2_A$ and $2_B$ that started according to FIG. 21 from the angles $\alpha_2$ and $\beta_2$, respectively.

It should be noted that for any scan position of the scanning unit 300 in the scan range determined between the scan positions of the scanning unit 300 illustrated by FIGS. 21 and 23, the collimator 302 is capable of passing the scanning primary axes, such as the axes $1_A$, $1_B$, $2_A$ and $2_B$ and blocking other non-scanning primary axes, such as the axes $3_A$, $4_A$, $5_A$, $3_B$, $4_B$ and $5_B$.

In the example of the scanning unit 300 of FIGS. 21-23, only the scanning angles with corresponding primary axes 18, such as those having indexes $1_A$ and $2_A$ directed to the right of the pixels 306 and $1_B$ and $2_B$ directed to the left of the pixel 306 are used for the scan. In this case, the primary axes 18 of FIGS. 10 and 14 passing through the pinholes 17 of plate 15 are arranged only along the frames 126 and 128 where a two dimensional scan is performed.

It should be noted that if the blocking-collimator 302, in the initial scan position 312 of FIG. 21, blocks the primary axes, such as the axes $3_A$, $4_A$, $5_A$, $3_B$, $4_B$ and $5_B$, then the collimator 302 is also capable of blocking these axes in any of the other scan position, such as the positions 318 and 324 of FIGS. 22 and 23, respectively. This is because the scanning angles of the primary axes $3_A$, $4_A$, $5_A$, $3_B$, $4_B$ and $5_B$ of FIGS. 22 and 23 are always shallower than the scanning angles of the primary axes $3_A$, $4_A$, $5_A$, $3_B$, $4_B$ and $5_B$ in the initial scanning of FIG. 21.

It should also be noted that while the blocking-collimator 302, of FIGS. 21-23, allows four primary scanning axes, such as the axes $1_A$, $2_A$, $1_B$ and $2_B$, to therethrough from the scanning plate 14 to the scanning plate 15, it may also allow any other number of scanning primary axes to pass therethrough from the plate 14 to the plate 15.

The scanning primary axes $1_A$, $2_A$, $1_B$ and $2_B$ corresponding to the scanning angles $\alpha_1$, $\beta_1$, $\alpha_2$ and $\beta_2$ and passing through the pinholes 16 of the plate 14 are displaced by the distances $\lambda/2$, $\lambda/2$, $3/2\lambda$ and $3/2\lambda$ from the center of the pixel 306, respectively. Since all the pinholes 16 are located at the same distance from the imaging plane 10, the following mathematical relationships is defined:

$$\tan(\alpha_2) = \tan(\beta_2) = 3 \cdot \tan(\alpha_1) = 3 \cdot \tan(\beta_1) \quad \text{Eq (9)}$$

As described above, the initial scanning angle of the axes $1_A$, $1_B$ is $\alpha_1 = \beta_1$ and the final scanning angle is $\alpha_2 = \beta_2$. Thus, relationships similar to those of Eq (9) apply also for the scanning axes $2_A$ and $2_B$ having initial scanning angles $\alpha_2 = \beta_2$ and final scanning angles $\alpha_5 = \beta_5$. Accordingly, the relationships between the initial and the final scanning angles of axes $2_A$ and $2_B$ is given by:

$$\tan(\alpha_5) = \tan(\beta_5) = 3 \cdot \tan(\alpha_2) = 3 \cdot \tan(\beta_2) \quad \text{Eq (10)}$$

In the specific examples of FIGS. 21-23, $\alpha_1 = \beta_1$, $\alpha_2 = \beta_2$ and $\alpha_5 = \beta_5$ are about 7°, 21° and 63°, respectively, representing large scanning angles. In this specific case, the axes $1_A$ and $1_B$ scan the range from 7 degrees to 21 degrees in clockwise and counterclockwise directions respectively. At the same time, the axes $2_A$ and $2_B$ scan the range from 21 degrees to 63 degrees in clockwise and counterclockwise directions respectively. This means that the scan range of the axes $1_A$, $2_A$, $1_B$ and $2_B$ is from 7 degrees to 63 degrees in clockwise and counterclockwise directions. Thus, the total scan range is $2\times(63-7)=112$ degrees.

It should be noted that the differences between the angles $\alpha_1 = \beta_1$, $\alpha_2 = \beta_2$ and $\alpha_5 = \beta_5$ depends on the initial value of $\alpha_1 = \beta_1$, which can be selected arbitrarily, by selecting the proper distances of the plates 14 and 15 from the imaging plane 10 of FIG. 10, to produce even larger scanning angles $\alpha_1 \beta_1$, $\alpha_2 = \beta_2$ and $\alpha_5 = \beta_5$.

From the description above, it should be clear that the scanning unit 300 in various embodiments, such as illustrated by FIGS. 21-23, may be characterized by:

1. High sensitivity.
2. Radiation from the imaged object may be collected by each pixel 34 via multiple pinholes 16 and multiple pinholes 17 of the plates 14 and 15, respectively.
3. The scanning plate 15 has one pinhole for each pixel.
4. High quality image reconstruction may be achieved using the scanning unit 300 since this unit does not produce redundant information and the data acquired with a scan unit, such as the scanning unit 300, may include multiple images that each is substantially different from the other images for each scanning position or angle. These images are produced by the detector 32 when collecting the radiation emitted from the surface of the imaged object and from the volume inside the imaged object. Accordingly, for any scan position, the radiation emitted from the imaged object is collected by the radiation detector 32 and is received from different regions on and in the imaged object. The ability to produce a different image, for any scan position of the scanning unit 300, taken from different regions of the radiation emitting object (imaged object) is mainly due to:

a. The collimation control of the scanning angles.
b. The blocking of the radiation paths, from the object to detector 32, which are oriented normal to imaging plane 10 of detector 32.

It should be noted that in the situation described in (b) above, only the radiation paths from the radiation emitting object to the detector 32 passing through the pinholes 16 and 17 of plates 14 and 15, respectively, which are oriented along the axes 18 that are tilted with respect to lines oriented normal to imaging plane 10 are used. Accordingly, all the inclination angles of the axes 18 as measured between the axes 18 and the references lines oriented normal to the imaging plane 10 are different from zero.

5. Even though there is no redundant information produced by the scanning unit 300, the scanning unit 300 is capable of scanning relatively large angles.
6. The scanning unit 300 performs the radiation scan in response to the relative positions between the plates 14 and 15, the collimator 302 and the imaging plane 10, by both, rotating the scanning angles as illustrated by the rotation of the lines 18 and changing the collimation angles of the solid scanning angles (corresponding to the primary axes 18). It should be clear that similar scanning properties of the scanning units 300 may be achieved when the plate 15 is replaced with the plate 14 to produce an alternative configuration where the plate 15 is placed between the imaging plane 10 and the plate 15.

Figure 24:
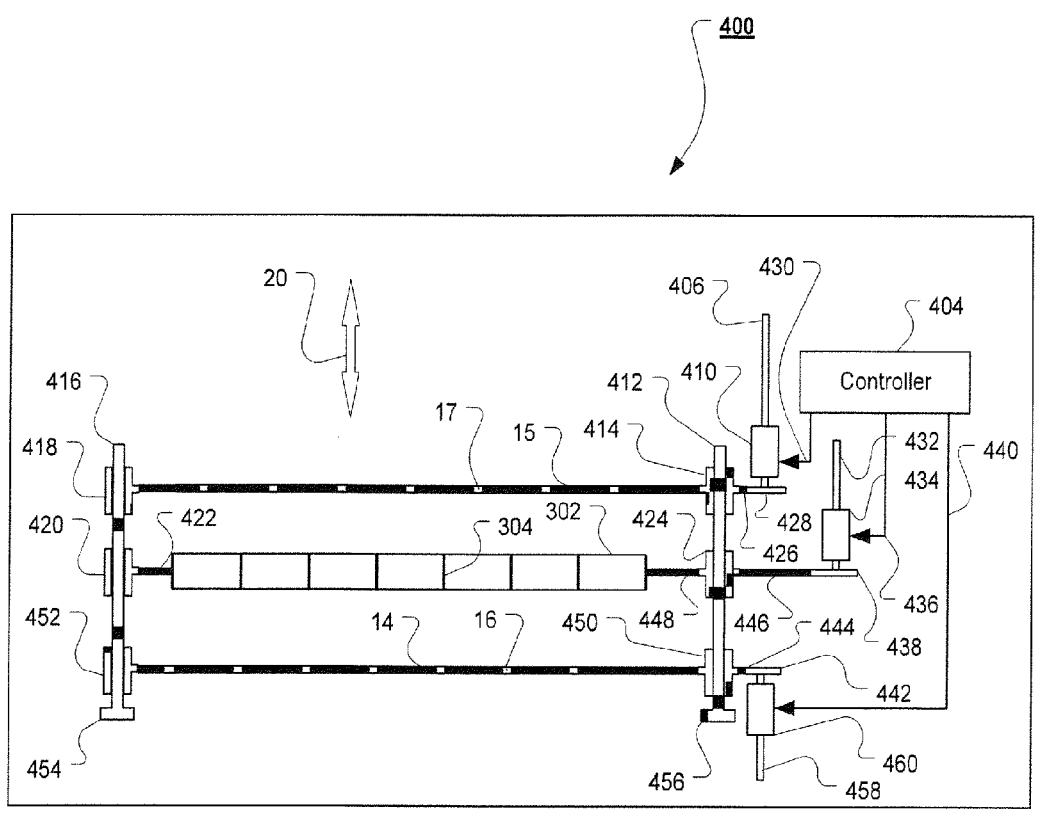
FIG. 24 is a schematic illustration of a radiation scanning unit including a mechanical unit configured to move two scanning plates and a partially radiation-blocking collimator using three motors in accordance with an embodiment.

FIG. 24 is a schematic side-view illustration of an electro-mechanics unit 400 designed to produce the scan motion of the plates 14 and 15 and the collimator 302. The electro-mechanics unit 400 includes posts 412 and 416 having mounting bases 456 and 454, respectively, for mounting the unit 400 above an imaging plane, such as the imaging plane 10 of FIG. 9 (not shown) for producing a radiation scanning camera-head. Sliding sleeves 452, 420 and 418 are coupled to the post 416 and sliding sleeves 450, 424 and 414 are coupled to the post 412.

The plate 15 having the pinhole array 17 is coupled to sliding sleeves 418 and 414 moving on the posts 416 and 412, respectively. The collimator 302 having septa 304 is attached, by arms 422 and 448, to the sliding sleeves 420 and 424 moving on the posts 416 and 412, respectively. The plate 14 having the pinhole array 16 is attached to the sliding sleeves 452 and 450 moving on the posts 416 and 412, respectively.

Driving motors 410, 434 and 460 having linearly moving axes 406, 432 and 458 and mounting plates 428, 438 and 442, respectively also may be provided. The plates 428, 438 and 442 of the motors 410, 434 and 460 are attached to the linearly moving axes 406, 432 and 458 and the sleeves 414, 424 and 450 by the arms 426, 446, and 444 for moving the plates 15, the collimator 302 and the plate 14 by linearly moving the axes 406, 432 and 458 of the motors 410, 434 and 460, respectively.

A controller 404 controls the motors 410, 434 and 460 via electrical leads 430, 436 and 440 to control the movement of the axes 406, 432 and 458 and thus, to control the linear scan, along the arrows 20, of the plates 14 and 15 and the collimator 302 for producing the angular scan of the primary axes such as the axes 18 of FIG. 9 passing through the pinholes 16, 17 of the plates 14 and 15, respectively, and between the septa 304 of the collimator 302.

Figure 25:
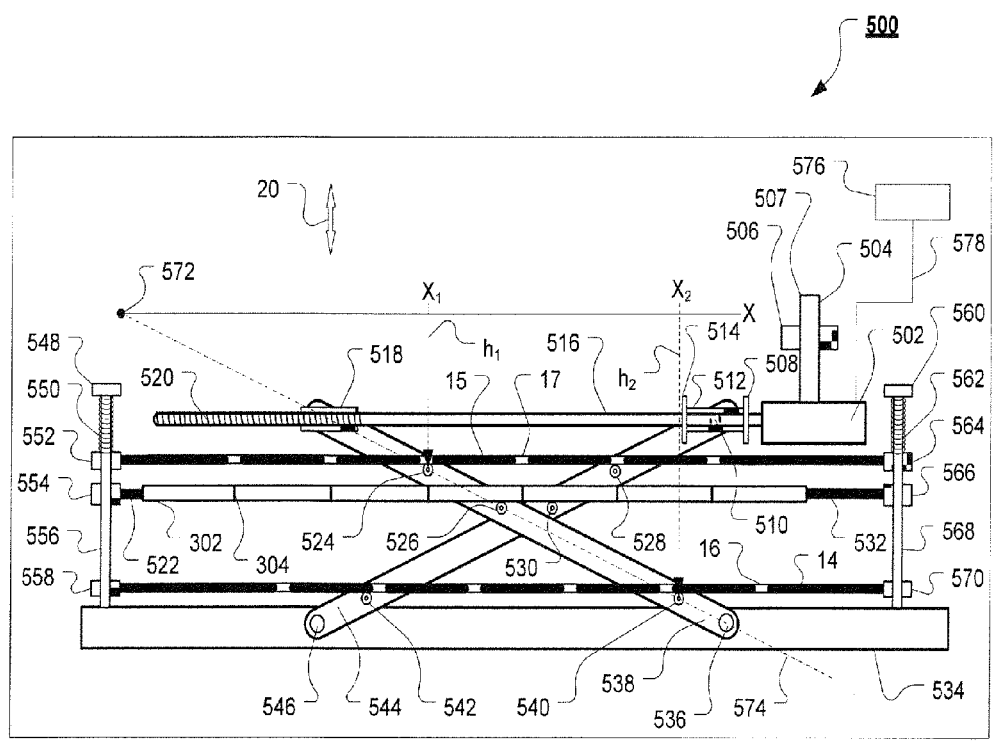
FIG. 25 is a schematic illustration of a radiation scanning unit including a mechanical unit configured to move two scanning plates and a partially radiation-blocking collimator using one motor in accordance with an embodiment.

FIG. 25 is a schematic illustration of an electro-mechanics scanning unit 500 designed to produce the linear scan of the plates 14 and 15 and the collimator 302 for producing an angular scan of the primary axes, such as the axes 18 of FIG. 9, by a configuration that is alternative to the configuration of the unit 400 of FIG. 24. The unit 500, unlike the unit 400 that has three driving motors, includes only one driving motor 502. The one driving motor 502 is still capable of moving the plates 14 and 15 and the collimator 302 while maintaining the relationships between the positions of the plates 14 and 15 and the collimator 302 as expressed by Eq (4).

The scan unit 500 of FIG. 25 includes a base 534 to which arms 538 and 544 are attached by axes 536 and 546, respectively. The other side of the arm 544 is attached, by the hidden axis 510, shown by broken lines, to a sliding sleeve 512. The other side of the arm 538 is attached, by the hidden axis, such as the axis 510 (not shown), to a nut 518. The axis 516 of the motor 502 passes by sleeve 512 and is screwed, by the screw 520 into the nut 518. The axis 516 is attached to disks 508 and 514 that rotate together with the axis 516 and are located to the right and to the left of the sleeve 512, respectively.

A mounting device 504 is attached, on one side, to the motor 502 and may slide up and down in the direction of the arrows 20 in an opening 507 of a stabilizer 506. The stabilizer 506 prevents the motor 502 from rotating, but allows the motor 502 to move up and down in the directions of the arrows 20. A post 556 on which the sliding sleeves 552, 554 and 558 move is inserted into the base 534. Similarly, a post 568 on which the sliding sleeves 564, 566 and 570 move is inserted into the base 534 as well. The base 534 supports a radiation detector (not shown), such as the detector 32 of FIG. 9 for producing a radiation scanning camera head. A spring 550 mounted on the post 556 is located between the sleeve 552 and a stopper 548 attached to the post 556. Similarly, a spring 562 mounted on the post 568 is located between the sleeve 564 and a stopper 560 attached to the post 568.

The plate 14 having the pinhole-array 16 is attached, on a left side to the sleeve 558, and on a right side to the sleeve 570 (as viewed in the Figure). The collimator 302 having the septa 304 is attached, by the arm 522, on the left side to the sleeve 554 and by the arm 532, on the right side, to the sleeve 566. The plate 15 having the pinhole-array 17 is attached, on the left side to the sleeve 552, and on the right side to the sleeve 564. The plate 14 is supported by wheels 540 and 542 rotatable around respective axes (not shown) and are inserted into the arms 538 and 544, respectively. The collimator 302 is supported by wheels 526 and 530 rotatable around respective axes (not shown) and are inserted into the arms 538 and 544, respectively. The plate 15 is supported by wheels 524 and 528 rotatable around respective axes (not shown) and are inserted into the arms 538 and 544, respectively.

When the motor 502 controlled by a controller 576 via electronics lead 578, rotates an axis 516 clockwise, a nut 518 is pulled to the right and a sleeve 512 is pushed, by disk 508, to the left. This causes the arms 538 and 544 to rotate clockwise and counterclockwise, respectively, in a way that the wheels 540, 542, 530, 526, 528 and 524 lift the plates 14 and 15 and the collimator 302. The wheels 540, 542, 530, 526 528 and 524 rotate while lifting the plates 14 and 15 and the collimator 302. The sleeves 558, 554 and 552 slide up and down on the post 556 and the sleeves 570, 566 and 564 slide up and down on the post 568, thus preventing lateral movement of the plates 14 and 15 and the collimator 302 while these components move up and down. The springs 550 and 562 are compressed by the sleeves 552 and 564 that move up toward the stoppers 548 and 560, respectively.

When the motor 502 rotates the axis 516 counter clockwise, the nut 518 is pushed to the left and the sleeve 512 is pulled, by the disk 514, to the right. This causes the arms 538 and 544 to rotate counterclockwise and clockwise, respectively, in a way that the wheels 540, 542, 530, 526 528 and 524 allow the plates 14 and 15 and the collimator 302 move down. The wheels 540, 542, 530, 526 528 and 524 rotate while allowing the plates 14 and 15 and the collimator 302 to move down. The plates 14 and 15 and the collimator 302 are forced to move down either, by the force of gravity or by loaded springs, such as the spring 550 that is compressed between the sleeve 552 and the stopper 548 and the spring 562 that is compressed between the sleeve 566 and the stopper 560, which push the plate 15 down. The sleeves 558, 554, 552, 570, 566 and 564 slide down on the posts 556 and 568 and thus prevent lateral movement of the plates 14 and 15 and the collimator 302 while these components move down.

A line 574 that passes through the wheels 540 and 524 also passes through a reference point 572. The coordinate X originated at the reference point 572 is directed parallel to the plates 14 and 15. The points $X_1$ and $X_2$ are coordinated by the supporting wheels 524 and 540 that determine the position of the plates 15 and 14, respectively. As can be seen, the distance of the plate 14 from the point $X_2$ is similar to distance $h_2$ and the distance of the plate 15 from the point $X_1$ is similar to distance $h_1$. It can be seen that the triangle that is defined by the corners located at the points 572, $X_1$ and 524 is similar to the triangle that is defined by the corners located at the points 572, $X_2$ and 540. Accordingly, the relationships according to Eq (4) are maintained for any scan position of the scanning unit 500.

The scanning unit 500 may be at a lowest scan position where the end of the screw 520 arrives at the nut 518. From this point, the scanning unit 500 can scan only upward when the motor 502 rotates the axis 516 clockwise. To increase the scan range of the unit 500, the arms 538 and 544 are displaced from each other, in a direction pointing into the plane of FIG. 25 by a distance larger than the thickness of the wheels 530 and 528 inserted into the arm 544. Such a displacement between the rotating arms 538 and 544 prevents the wheels 530 and 528 from colliding with the arm 538.

Figure 26:
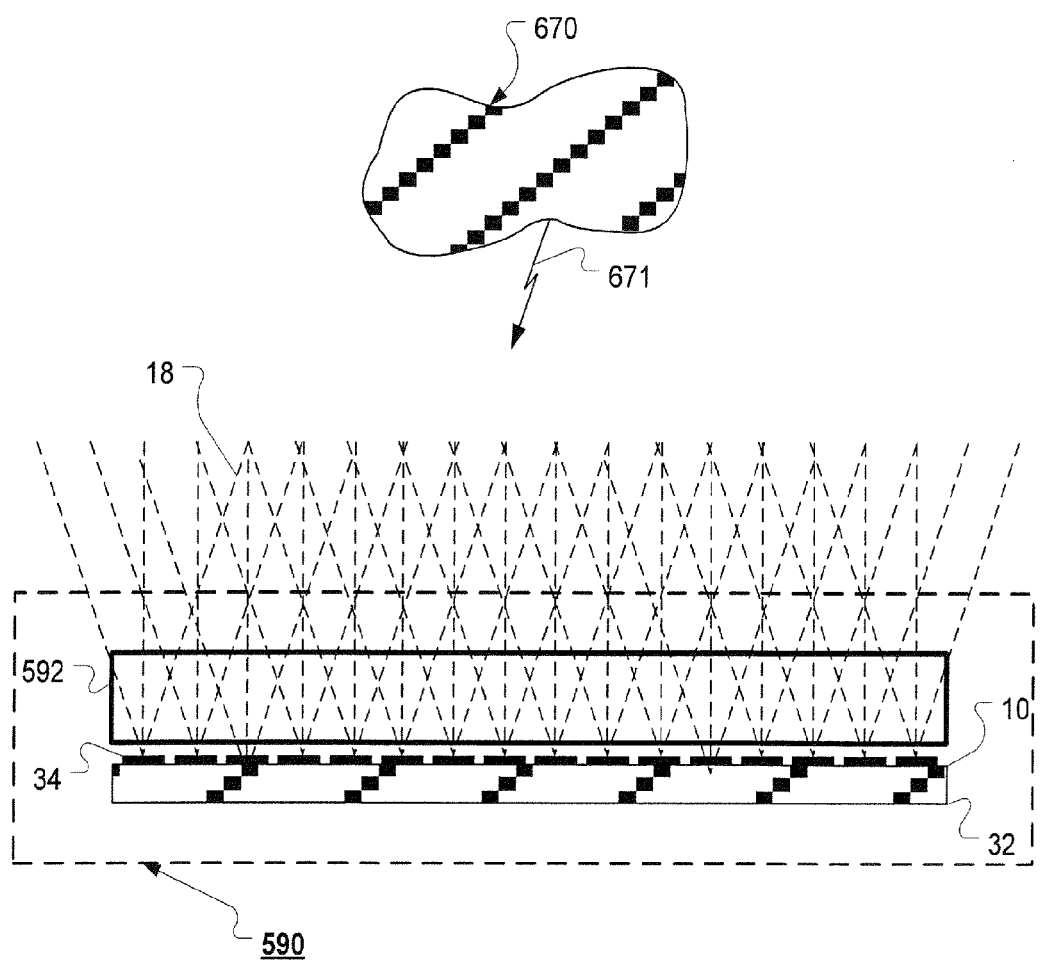
FIG. 26 is a schematic illustration showing a radiation scanning camera-head including a radiation detector integrated with radiation scanning unit in accordance with various embodiments.

FIG. 26 schematically illustrates a radiation scanning camera head 590 including a scanning unit 592 mounted between a pixelated detector or the array of pixelated detectors 32 of FIG. 9 and a radiation emitting object 670. The radiation scanning camera receives radiation 671 emitted from an object 670 along radiation paths directed along the axes 18, such as the axes 18 of FIGS. 21-23. The radiation paths from the object 670 to the detector 32, directed along the axes 18, start at the object 670 and propagate from there through the arrays of pinholes 16 and 17 of the plates 14 and 15, respectively. The plates 14 and 15 are included in the scanning unit 592 (not shown in FIG. 26 but, are illustrated in the scanning unit 300 of FIGS. 21-23). The lines 18 are the primary axes of the scanning solid angles of the scanning unit 592 similar to the scanning angles 54, 56, 54' and 56' of FIG. 8 and the scanning angles 72, 74, 76 and 78 of FIG. 9 by which the camera head 590 collects, onto the detector 32, radiation 671 emitted from the object 670. The array of detectors 32 have a two dimensional array of pixels 34 forming the imaging plane 10. The scanning unit 592 may be configured as described for the scanning units 400 and 500 of FIGS. 24 and 25, respectively. The mounting components of the scanning unit 592 that hold the scanning unit 592 above the imaging plane 10 are not shown.

Similar to FIGS. 8 and 21-23, the orientation of the lines 18, along which the scanning camera head 590 collects or acquires the radiation emitted from the object 670 rotate clockwise and counterclockwise in response to a bidirectional linear scan of the plates 14 and 15 moving in the directions of the arrows 20 oriented normal to the imaging plane 10. As can be seen from FIGS. 21-23 and 26, each pixel 34 receives radiation from an imaged object emitting radiation along multiple radiation paths from the object to the radiation detector 32 via the pinholes 16 and 17 of the plates 14 and 15, respectively. These radiation paths are aligned along the lines 18 which are the primary axes of the scanning angles by which the radiation detector 32 receives radiation 671 from the radiation emitting object 670. Because multiple radiation paths along the lines 18 are collected by each pixel 34, the radiation scanning camera 590 produces a scan with high sensitivity.

Figure 27:
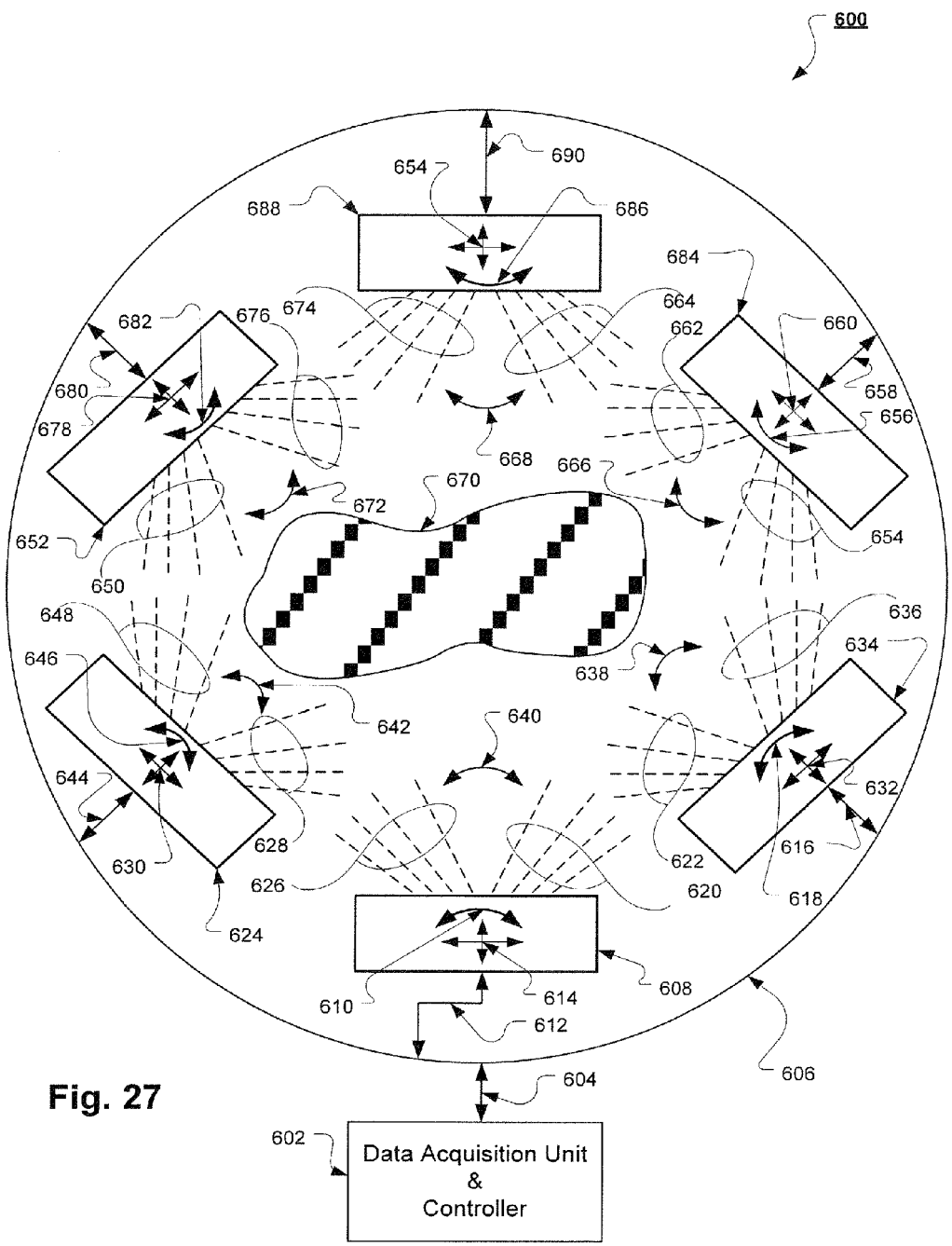
FIG. 27 is a diagram illustrating a Single Photon Emission Computed Tomography (SPECT) system including multiple radiation scanning camera-heads in accordance with various embodiments.

FIG. 27 is a schematic illustration of a SPECT system 600 including multiple radiation scanning camera-heads 608, 624, 652, 688, 684, and 634. The camera heads 608, 624, 652, 688, 684, and 634 are radiation scanning cameras, such as of the radiation scanning camera 590 illustrated by FIG. 26. Each of the camera heads 608, 624, 652, 688, 684 and 634 produces an angular scan of the radiation emitted from the object 670. The object 670 is the radiation source of the system 600 and may be a patient that was treated by injection of radioactive isotopes/tracers. For the clarity of FIG. 27, the density of the radiation emitted from the object 670 is not shown. However, the radiation paths along which the radiation scanning cameras collect the radiation emitted from the object 670 are still illustrated. For example, the camera head 608 collects the radiation emitted from the object 670 along the orientations shown by the broken lines 620 and 626. The groups of broken lines 620 and 626, along which the radiation emitted from the object 670 is collected by the camera head 608, represent the scan orientations of clockwise and counter clockwise angular scanning rotating in the directions of the arrows 640. Similarly, the camera heads 624, 652, 688, 684, and 634 have pairs of scanning groups (628, 648), (650, 676), (674, 664), (662, 654) and (636, 622) rotating clockwise and counter clockwise in the direction of the arrows 642, 672, 668, 666 and 638, respectively. These pairs of scanning groups are similar to groups of scanning lines/primary axes 18 of FIGS. 21-23 and 26.

The use of angular scanning, such as the one illustrated by the groups 620 and 626 allows operation in SPECT and three-dimensional (3D) reconstruction of the image of the scanned object 670, even when only a single and static camera head, such as one of the camera-heads 608, 624, 652, 688, 684, and 634, is used. Even though, only one camera head such as the head 608 is enough for producing SPECT, several camera-heads, such as the cameras 608, 624, 652, 688, 684, and 634, which scan the object 670 from different viewing angles, may be used to improve the image quality and reduce the acquisition time.

In some embodiments of the scanning/SPECT system 600, each of the cameras 608, 624, 652, 688, 684, and 634 may further include two dimensional linear-movements along the arrows of the Cartesian coordinates systems 614, 630, 678, 654, 660 and 632 and rotational movements along the arrows 610, 646, 682, 686, 656 and 618, respectively. The types of movements, such as the rotational movements and the two dimensional linear-movements may be applied to the camera heads 608, 624, 652, 688, 684, and 634 either as separate types of movements or as a combined movement including both types of the movements concurrently or simultaneously.

In one embodiment, the data acquisition unit and controller 602, and the camera heads 608, 624, 652, 688, 684, and 634 are connected to a bidirectional Local Area Network (LAN) 606 by bidirectional ports 604, 612, 644, 680, 690, 658, and 616, respectively. The LAN 606 transmits to the data acquisition and controller unit 602 the scanned data from the camera heads 608, 624, 652, 688, 684, and 634 for reconstructing three dimensional images of the radiation emitted from the object 670. The information about the positions of the cameras 608, 624, 652, 688, 684, and 634 received from the decoders of these cameras (not shown) is also transmitted, by the LAN 606 to the data acquisition and controller unit 602 via the bidirectional ports 604, 612, 644, 680, 690, 658, and 616, respectively. The commands controlling the driving motors (not shown) that produce the linear movement and rotational motion of cameras 608, 624, 652, 688, 684, and 634 are sent in a direction opposite to that described above from the data acquisition and controller unit 602 through the LAN 606 and via the ports 604, 612, 644, 680, 690, 658, and 616. The data acquisition and controller unit 602 may send control commands to control the position of the scanning camera heads 608, 624, 652, 688, 684, and 634 in response to the data acquired by these camera-heads and received in the unit 602.

While FIGS. 10, 12 and 14-16 shown the pinhole-arrays 16 and 17 as having square pinholes, it should be noted that the shape of the pinholes may have different shapes, such as, slits and or circular pinholes. Also, while the scan unit 300 of FIG. 21 shows ten primary axes representing the ten scanning angles via which the pixel 306 views the imaged or scanned object, there is no limit on the number of the scanning angles that each pixel in the imaging plane 10 may have. Additionally, while only the pixel 306 is shown in FIG. 21 as having scanning angles, it should be clear that each of the pixels 34 in the imaging plane 10 has similar scanning angles.

Further, while FIG. 21 illustrates that each pixel 34 uses four scanning angles (two to the right and two to the left of the pixel), it should be clear that there is no limitation on the number of scanning angles that each pixel 34 uses. Also, while FIG. 21 shows that the collimator 302 blocks six viewing angles for each pixel (three to the right and three to the left of each pixel), it should be clear that there is no limitation on the number of scanning angles that the collimator 302 blocks for each pixel.

Moreover, while the plate 14 is illustrated as positioned between the imaging plane 10 and the plate 14, it should be clear that the plate 15 may be positioned between the imaging plane 10 and the plate 14. Also, while the plates 14, 15 and the collimator 302 are illustrated as being driven by a motor or motors, to produce linear scan, it should be clear that the plates 14, 15 and the collimator 302 may be driven by a variety of motors such as DC or stepping motors or may be driven by other means such as magnetic, electrostatic, hydraulic or pneumatic manipulators.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A system for scanning and collecting ionizing radiation emitted from an object, the system comprising:
at least one radiation scanning camera-head;
an array of at least one pixelated radiation detector having an imaging surface including a two-dimensional array of pixels; and
a scanning unit positioned between the pixelated radiation detector and the object, the scanning unit including:
a first and a second radiation blocking plates having first and second two-dimensional arrays of openings, respectively, wherein the two-dimensional array of pixels and the first and the second two-dimensional arrays of openings have a same pitch, projections of openings of the first two-dimensional array onto the imaging surface of the pixelated radiation detector are two-dimensionally aligned with border lines between adjacent pixels, projections of openings of the second two-dimensional array onto the imaging surface of the pixelated radiation detector are aligned with centers of pixels of the pixelated radiation detector; and
a movable collimator positioned between the first and the second pinhole radiation blocking plates, the movable collimator having a septa with a two-dimensional array of channels, the first and second radiation blocking plates and the movable collimator are coupled to first and second sleeves that traverse along posts preventing lateral movement of the first and second radiation blocking plates and the movable collimator, the first and second radiation blocking plates and the movable collimator are movable along a direction normal to the imaging plane to perform a linear scan of the scan unit, wherein for each of a plurality of scan positions of the scanning unit, relative positions between the first and second radiation blocking plates, the movable collimator, and the imaging surface are differently adjusted to produce with respect to each other to produce different radiation paths from the object to the pixelated radiation detector via the first and second two-dimensional array of openings and the septa at each scan position, the different radiation paths oriented along lines forming inclination angles with lines oriented normal to the imaging surface.

2. The system of claim 1, wherein the system is a Single Photon Emission Computed Tomography (SPECT) system.

3. The system of claim 1, wherein the first and second radiation blocking plates are configured to move along a line directed normal to the imaging surface to produce a linear scan of the first and second radiation blocking plates.

4. The system of claim 3, further comprising a plurality of motors that move the first and second radiation blocking plates in a direction normal to the surface of the pixelated radiation detector to perform the linear scan.

5. The system of claim 4, wherein the motors move the first and second radiation blocking plates and the movable collimator linearly and continuously.

6. The system of claim 4, wherein the motors move the first and second radiation blocking plates and the movable collimator step-by-step.

7. The system of claim 3, further comprising a single motor that moves the first and second radiation blocking plates and the movable collimator in a direction normal to the surface of the pixelated radiation detector to perform the linear scan.

8. The system of claim 7, wherein the motor moves the first and second radiation blocking plates and the movable collimator linearly and continuously.

9. The system of claim 7, wherein the motor moves the first and second radiation blocking plates and the movable collimator step-by-step.

10. The system of claim 1, wherein the radiation emitted from the object is collected by the pixelated radiation detector along lines passing through the first and the second two-dimensional arrays of openings and the septa.

11. The system of claim 10, wherein the radiation emitted from the object is collectable by every pixel in the two-dimensional array of pixels of the pixelated radiation detector along multiple lines passing through the first and the second two-dimensional arrays of openings and the septa.

12. The system of claim 10, wherein orientations of the lines along which the detector collects the radiation from the object are based on a scan position of the linear scan.

13. The system of claim 10, wherein the lines includes first and second groups of the lines, wherein in response to the linear scan of the first and second radiation blocking plates and the movable collimator, the lines produce a two dimensional angular scan wherein the orientations of the first group of the lines rotate clockwise and the orientations of the second group of the lines rotate counterclockwise such that each pixel of the pixelated radiation detector collects a pair of radiation paths at each two dimensional direction.

14. The system of claim 13, wherein for each position of the two dimensional angular scan of the lines and for each position of the linear scan of the first and second radiation blocking plates and the movable collimator, the radiation emitted from the object is collected by the pixelated radiation detector from different regions on and in the object.

15. The system of claim 13, wherein for any scan position of the two dimensional angular scan, all of the lines are tilted with respect to lines directed normal to the surface of the pixelated radiation detector and wherein the inclination angles of the lines are not zero.

16. The system of claim 1, wherein the pixelated radiation detector is made of Cadmium Zinc Telluride (CZT).

17. The system of claim 1, wherein the first and second radiation blocking plates are made of radiation blocking materials selected from the group of materials consisting of Lead (Pb) and Tungsten (W).

18. The system of claim 1, wherein the first and the second two-dimensional array of openings includes openings that are at least one of square, circular or slit openings.

19. The system of claim 1, wherein the first and the second two-dimensional array of openings is an array of slits, and the first radiation blocking plate includes a supporting substrate that is substantially transparent to the ionizing radiation.

20. The system of claim 1, further comprising at least one motor and wherein the movable collimator located between the first and second radiation blocking plates is arranged to produce a linear scan and is moved by the at least one motor.

21. The system of claim 1, wherein the at least one radiation scanning camera-head is configured to move along coordinates of a Cartesian coordinates system.

22. The system of claim 1, wherein the at least one radiation scanning camera-head is configured to produce a rotational motion.

23. The system of claim 1, wherein the at least one radiation scanning camera-head is configured to move along coordinates of a Cartesian coordinates system and to produce a rotational motion.

24. A method for scanning and collecting ionizing radiation emitted from an object, the method comprising:
configuring a scanning unit to be positioned between a radiation detector and an object, the scanning unit including:
a first and a second radiation blocking plates having first and second two-dimensional arrays of openings, respectively, wherein an array of pixels and the first and the second two-dimensional arrays of openings have a same pitch, projections of openings of the first two-dimensional array onto an imaging surface of the radiation detector are two-dimensionally aligned with border lines between adjacent pixels, projections of openings of the second two-dimensional array onto the imaging surface of the radiation detector are aligned with centers of pixels of the radiation detector; and
a movable collimator positioned between the first and the second pinhole radiation blocking plates, the movable collimator having a septa with a two-dimensional array of channels, the first and second radiation blocking plates and movable collimator are coupled to first and second sleeves that traverse along posts preventing lateral movement of the first and second blocking plates and movable collimator, the first and second radiation blocking plates and movable collimator are movable along a direction normal to an imaging plane to perform a linear scan of the scanning unit; and
controlling the scanning unit to position the first and second radiation blocking plates, the movable collimator, and the imaging surface, for each of a plurality of scan positions of the scanning unit, differently with respect to each other to produce different radiation paths from the object to the pixelated radiation detector via the first and second two-dimensional array of openings and the septa at each scan position, the different radiation paths oriented along lines forming inclination angles with lines oriented normal to the imaging surface.

25. The method of claim 24, further comprising controlling the scanning unit to move the first and second radiation blocking plates and the movable collimator along a line directed normal to the imaging surface to produce a linear scan of the first and second radiation blocking plates.

26. The method of claim 25, wherein the scanning unit comprises one or more motors and controlling the scanning unit further comprises controlling movement of the first and second radiation blocking plates and the movable collimator in a direction normal to the imaging surface of the radiation detector to perform the linear scan.

27. The method of claim 26, wherein the movement is linear and continuous.

28. The method of claim 26, wherein the motors move the first and second radiation blocking plates and the movable collimator step-by-step.

29. The method of claim 25, wherein controlling the scanning unit including controlling the scanning unit to at least one of move at least one radiation scanning camera-head along coordinates of a Cartesian coordinates system or to produce a rotational motion.

\* \* \* \* \*